(12) United States Patent
Peters et al.

(10) Patent No.: US 12,391,627 B2
(45) Date of Patent: Aug. 19, 2025

(54) GENETICALLY MODIFIED NITROGEN FIXING BACTERIA AND USES THEREOF

(71) Applicants: Wisconsin Alumni Research Foundation, Madison, WI (US); Washington State University, Pullman, WA (US)

(72) Inventors: John Peters, Pullman, WA (US); Florence Mus, Pullman, WA (US); Jean-Michel Ané, Madison, WI (US); Devanshi Khokhani, Madison, WI (US)

(73) Assignees: WISCONSIN ALUMNI RESEARCH FOUNDATION, Madison, WI (US); WASHINGTON STATE UNIVERSITY, Pullman, WA (US)

(*) Notice: Subject to any disclaimer, the term of this patent is extended or adjusted under 35 U.S.C. 154(b) by 1230 days.

(21) Appl. No.: 17/024,746

(22) Filed: Sep. 18, 2020

(65) Prior Publication Data
US 2021/0107844 A1   Apr. 15, 2021

Related U.S. Application Data

(60) Provisional application No. 63/056,050, filed on Jul. 24, 2020, provisional application No. 63/018,551, filed on May 1, 2020, provisional application No. 62/902,219, filed on Sep. 18, 2019.

(51) Int. Cl.
| | |
|---|---|
| C05F 11/08 | (2006.01) |
| C12N 1/20 | (2006.01) |
| C12N 15/74 | (2006.01) |

(52) U.S. Cl.
CPC ............... *C05F 11/08* (2013.01); *C12N 1/20* (2013.01); *C12N 15/74* (2013.01)

(58) Field of Classification Search
CPC ............ C05F 11/08; C12N 1/20; C12N 15/74
See application file for complete search history.

(56) References Cited

FOREIGN PATENT DOCUMENTS

WO   93/05154 A1   3/1993

OTHER PUBLICATIONS

Gholiloo et al. (Jounral of Plant Nutrition, vol. 42 No. 13, pp. 1417-1429) (Year: 2019).*
Ortiz-Marquez et al. (Applied and Environmental Microbiology, pp. 2345-2352) (Year: 2012).*
Ambrosio et al. (Metabolic Engineering, vol. 40, pp. 59-68) (Year: 2017).*
Bertani G (1951) "Studies on lysogenesis I: the mode of phage liberation by lysogenic *Escherichia coli*1." J Bacteriol 62(3):293.
Jacobson, et al., "Physical and Genetic Map of the Major nif Gene Cluster from Azotobacter vinelandii", Journal of Bacteriology, 171(2): 1017-1027, 1989.
Johnson, et al., "Controlled Expression and Functional Analysis of iron-Sulfur Cluster Biosynthetic Components within Azotobacter vinelandii", Journal of Bacteriology, 188(21): 7551-7561, 2006.
Moshiri, et al., "Cloning, Characterization, and Expression in *Escherichia coli* of the Genes Encoding the Cytochrome d Oxidase Complex from Azotobacter vinelandii" Journal of Bacteriology, 173(19): 6230-6241, 1991.
Page, et al., "Induction of transformation competence in Azotobacter vinelandii iron-limited cultures" Can J Microbiol. Dec. 1978;24(12):1590-4. doi: 10.1139/m78-254. PMID: 747819.
Page, et al., "Optimal conditions for transformation of Aztobacter vinelandii" J of Bacteriology, 139(3): 1058-1061, 1979.
Premakumar, et al., "Effect of amino acid substitutions in a potential metal-binding site of AnfA on expression from the anfH promoter in Azotobacter vinelandii" J of Bacteriology, 176(19): 6139-6142, 1994.
Rey, et al., "Cytochrome c Terminal Oxidase Pathways of Azotobacter vinelandii: Analysis of Cytochrome c4 anc5 Mutants and Up-Regulation of Cytochrome c-dependent Pathways with N2 Fixation", Journal of Bacteriology, 179 (22):7191-7196, 1997.
Setubal, et al., "Genome Sequence of Azotobacter vinelandii, an Obligate Aerobe Specialized to Support Diverse Anaerobic Metabolic Processes", J Bacteriology, 191(14): 4534-4545, 2009.
Toukdarian, et al., "Regulation of nitrogen metabolism in Azotobacter vinelandii: isolation of ntr and glnA genes and construction of ntr mutants." The EMBO Journal, 5(2):399-407, 1986.
Brett Brewin et al: "The Basis of Ammonia Release in nifL Mutants of Azotobacter vinelandii," Journal of Bacteriology, vol. 181, No. 23, Dec. 1, 1999 (Dec. 1, 1999), pp. 7356-7362.

(Continued)

*Primary Examiner* — Robert A Zeman
(74) *Attorney, Agent, or Firm* — Quarles & Brady, LLP

(57) ABSTRACT

A genetically modified bacterium for excreting fixed nitrogen (in the form of ammonia) is disclosed. The bacterium can be made by deleting at least a portion of the nifL gene of a diazotrophic γ-proteobacterium, and inserting a promoter sequence into the diazotrophic γ-proteobacterium genome that is placed and oriented to direct transcription of the rnf1 gene complex. The resulting genetically modified bacterium excretes ammonia constitutively and at a greater rate than the wild type bacterium, and can be used to make biofertilizers to stimulate plant growth. The biofertilizers may contain a culture of the bacteria, or a co-culture of the bacteria and a mycorrhizal fungus.

15 Claims, 12 Drawing Sheets

Specification includes a Sequence Listing.

(56) References Cited

OTHER PUBLICATIONS

Anil Bali et al: "Excretion of Ammonia by a nifL Mutant of Azotobacter vinelandii Fixing Nitrogen," Applied and Environmental Microbiology, May 1, 1992 (May 1, 1992), pp. 1711-1718.
Bhat et al., "Nitrogen Fixing Biofertilizers; Mechanism and Growth Promotion: A Review", Journal of Pure and Applied Microbiology, vol. 9(2), pp. 1675-1690, Jun. 30, 2015 (Jun. 30, 2015).

* cited by examiner

SEQUENCE LISTING

<160> NUMBER OF SEQ ID NOS: 9

<210> SEQ ID NO 1
<211> LENGTH: 50
<212> TYPE: DNA

```
<213> ORGANISM: Artificial Sequence
<220> FEATURE:
<223> OTHER INFORMATION: PCR primer

<400> SEQUENCE: 1
ggaattccat atgcgattaa ggtgcggcac aggatttgct aatcttctct        50

<210> SEQ ID NO 2
<211> LENGTH: 40
<212> TYPE: DNA
<213> ORGANISM: Artificial Sequence
<220> FEATURE:
<223> OTHER INFORMATION: PCR primer

<400> SEQUENCE: 2
cccaagctta acttgcccett ttccacctcg ctttccaggt                  40

<210> SEQ ID NO 3
<211> LENGTH: 33
<212> TYPE: DNA
<213> ORGANISM: Artificial Sequence
<220> FEATURE:
<223> OTHER INFORMATION: PCR primer

<400> SEQUENCE: 3
cccggatccg tcgagctccc gggaagcttc tcg                          33

<210> SEQ ID NO 4
<211> LENGTH: 53
<212> TYPE: DNA
<213> ORGANISM: Artificial Sequence
<220> FEATURE:
<223> OTHER INFORMATION: PCR primer

<400> SEQUENCE: 4
tgcggtcgac gcgaaacgat cctcatcctg tctcttgatc agatcttgat ccc    53

<210> SEQ ID NO 5
<211> LENGTH: 45
<212> TYPE: DNA
<213> ORGANISM: Artificial Sequence
<220> FEATURE:
<223> OTHER INFORMATION: PCR primer

<400> SEQUENCE: 5
ccggaattcc tgcaggtagc cgaacacctc caggtcccgc cttcc             45

<210> SEQ ID NO 6
<211> LENGTH: 43
<212> TYPE: DNA
<213> ORGANISM: Artificial Sequence
<220> FEATURE:
<223> OTHER INFORMATION: PCR primer

<400> SEQUENCE: 6
tcccccggga ctccggcgca tttctagcgg ccgccgaagt tct               43

<210> SEQ ID NO 7
<211> LENGTH: 38
<212> TYPE: DNA
<213> ORGANISM: Artificial Sequence
<220> FEATURE:
<223> OTHER INFORMATION: PCR primer

<400> SEQUENCE: 7
gccgacgtcg accgtggctg attacgtgcg cccgcggc                     38
```

```
<210> SEQ ID NO 8
<211> LENGTH: 38
<212> TYPE: DNA
<213> ORGANISM: Artificial Sequence
<220> FEATURE:
<223> OTHER INFORMATION: PCR primer

<400> SEQUENCE: 8
gccgacgtcg accgtggctg attacgtgcg cccgcggc                            38

<210> SEQ ID NO 9
<211> LENGTH: 42
<212> TYPE: DNA
<213> ORGANISM: Artificial Sequence
<220> FEATURE:
<223> OTHER INFORMATION: PCR primer

<400> SEQUENCE: 9
ggggaattcc attccgcccg acctggtgct gaaggtgttc ga                       42
```

GENETICALLY MODIFIED NITROGEN FIXING BACTERIA AND USES THEREOF

CROSS-REFERENCE TO RELATED APPLICATIONS

This application claims the benefit of U.S. provisional Application No. 62/902,219, filed Sep. 18, 2019; U.S. provisional Application No. 63/018,551, filed May 1, 2020; and U.S. provisional Application No. 63/056,050, filed Jul. 24, 2020. Each of these applications is incorporated by reference herein in its entirety.

STATEMENT REGARDING FEDERALLY SPONSORED RESEARCH OR DEVELOPMENT

This invention was made with government support under 1753917 awarded by the National Science Foundation. The government has certain rights in the invention.

FIELD OF THE INVENTION

This disclosure relates generally to synthetic diazotrophic γ-proteobacteria that are genetically modified to exhibit an increased ability to fix atmospheric nitrogen in the form of excreted ammonia, as well as to methods of making and using such bacteria.

BACKGROUND OF THE INVENTION

Nitrogen is an essential element of biological molecules and of life on earth. Nitrogen is prevalent in the earth's atmosphere, where it exists as biologically inaccessible $N_2$. Limited access to fixed (bioavailable) forms of nitrogen in the soil, such as ammonia ($NH_3$), limits the productivity of crop plants and thus the production of food, feed, fiber and fuel.

Nitrogenous fertilizers chemically synthesized using the Haber-Bosch process are a major source for bioavailable nitrogen in the soil, and have become essential in modern agriculture for increasing crop yields and for replacing nitrogen removed from the system at harvest. However, the process of synthesizing chemical fertilizers is very energy intensive. With the increasing global population and significant problems caused by unintended nitrogen waste and pollution, more sustainable alternatives to are needed to the use of chemical fertilizers for providing bioavailable nitrogen and managing the nitrogen cycle in the soil.

Biological nitrogen fixation (diazotrophy), or the bioconversion of biological inaccessible $N_2$ to a biologically accessible form, such ammonia, is solely a microbial process. It does not occur in plants or animals. Some plants, including most legumes and a few non-legumes, form intimate nitrogen-fixing symbioses with diazotrophs, and in the process provide the plants with ammonia. As a consequence, legumes have been an integral part of sustainable agricultural systems for thousands of years.

Unfortunately, many important food species, including staple cereal grains such as maize/corn, rice and wheat, cannot establish effective nitrogen-fixing symbioses with diazotrophs. Accordingly, the production of such crops in the high yields required for modern commercial agriculture is still largely dependent on the application of nitrogenous fertilizers.

Growing evidence has suggested that free-living microbes (those that do not form intimate symbiotic relationships with plants) can provide fixed nitrogen to plants under certain conditions. Typically, nitrogen fixation in microorganisms not involved in symbiosis is tightly regulated, such that only the ammonia essential for optimal microbial metabolism is produced. This regulation typically occurs through a complex molecular mechanism where a protein functions to sense ammonia and other metabolites and acts to control a transcriptional activator of the genes for the enzyme responsible for nitrogen fixation.

Overcoming the negative regulatory control of ammonia (or other forms of fixed nitrogen) on nitrogenase synthesis in a manner that results in a microbial strain that produces the enzymes in excess, resulting in the production of an overabundance of ammonia and ammonia excretion, has been reported. However, such reports all involve the introduction of a trans gene in a specific manner within a specific site. Given the regulatory and environmental concerns associated with releasing organisms containing trans genes into the environment, these reported strategies cannot be used for fixing nitrogen on a commercial scale. Furthermore, it has not been demonstrated that such strategies can be successfully used to deliver biologically available nitrogen to plants that are not known to form symbiotic relationships with diazotrophs.

Accordingly, there is a need in the art for novel diazotrophs capable of excreting large amounts of ammonia without negative regulatory control that (1) do not contain a trans gene, and (2) can successfully facilitate the transfer of the ammonia to plants that are not known to form symbiotic relationships with diazotrophs.

BRIEF SUMMARY OF THE INVENTION

We have generated genetically-modified ammonia excreting strains of diazotrophic gamma-proteobacteria. In addition to demonstrating that such strains constitutively excrete large amounts of ammonia, we have also demonstrated that such strains can facilitate transfer of the excreted ammonia to non-leguminous crop plants. Accordingly, such bacterial strains can be incorporated into biofertilizers that can deliver fixed nitrogen to a wide range of crop plants.

In addition, we have demonstrated that the bacterial strains can transfer the fixed nitrogen (in the form of ammonia) to mycorrhizal fungi, which can further facilitate the transfer of the fixed nitrogen to non-leguminous crop plants. Accordingly, the bacterial strains together with one or more mycorrhizal fungi can also be incorporated into biofertilizers for delivering fixed nitrogen to a wide range of crop plants.

The genetic modifications for producing the ammonia excreting strains involve one or more deletions within the nifL gene, along with the insertion within the genome of a copy of a promoter that is placed and oriented to direct transcription of the rnf1 gene complex.

In an exemplary (and non-limiting) embodiment using *Azotobacter vinelandii*, the inserted promoter may be placed within the deleted nifL region of the genome and oriented to direct transcription upstream, opposite of the direction transcription is normally directed by the native nifL promoter in its "wild type" location. Because of the location and orientation of the rnf1 gene complex relative to the nifL gene in *Azotobacter vinelandii*, such an insertion would successfully direct rnf1 gene expression.

As the skilled artisan would understand, the inserted promoter placement and orientation needed to successfully direct rnf1 gene expression would vary among different diazotrophic γ-proteobacteria species, because the location and orientation of the rnf1 gene complex relative to the nifL gene varies among species. This disclosure encompasses all such promoter placements and orientations.

Notably, the amount or rate of ammonia excreted is correlated with the strength of the promoter that is inserted. In embodiments that do not include a trans gene, the inserted promoter is a copy of a native promoter that occurs elsewhere in the genome of the wild type bacterium.

According, in a first aspect, this disclosure encompasses genetically modified diazotrophic γ-proteobacterium exhibiting an increased ability to fix atmospheric nitrogen. The bacterium includes (a) one or more deletions within the nifL gene coding region of a wild type diazotrophic γ-proteobacterium; and (b) one or more insertions within the diazotrophic γ-proteobacterium genome of a promoter sequence. The promoter sequence is placed and oriented to direct transcription of the rnf1 gene complex. As a direct result of its placement and orientation, the inserted promoter (or promoters) acts to upregulate the expression of the rnf1 gene complex. The genetically modified diazotrophic γ-proteobacterium is capable of fixing nitrogen at a faster rate or to a greater degree than a wild type diazotrophic γ-proteobacterium.

In some embodiments, the promoter or promoters are inserted within the deleted nifL gene region and oriented in the opposite direction of nifL/nifA transcription, thus directing transcription in the upstream direction, away from the nifA gene. This is opposite the direction in which the nifL promoter directs transcription in its "wild type" position in the genome. In such embodiments, the promoter placement and orientation directs transcription towards the rnf1 gene complex (i.e., upstream relative to the nifL gene) and in its normal direction of transcription (i.e., opposite of the direction of transcription of the nifL/nifA genes).

In some embodiments, the rnf1 gene complex includes one or more genes from among rnfA1, rnfB1, rnfC1, rnfD1, rnfE1, rnfG1 or rnfH1.

In some embodiments, the bacterium is configured to constitutively synthesize the nitrogenase enzyme, so as to reduce nitrogen to ammonia even in the presence of ammonia in the surrounding environment. In some such embodiments, the upregulation of the expression of the rnf1 gene complex reduces Ferredoxin/Flavodoxin to feed the nitrogenase enzyme.

In some embodiments, at least one of the deletions and at least one of the promoter insertions are within the nifL gene.

In some embodiments, at least one of the deletions and at least one of the promoter insertions are within the N-terminal (PAS1 and PAS2 motifs) region of the nifL gene.

In some embodiments, at least one of the deletions and at least one of the promoter insertions are within the C-terminal (GHKL nitrogen sensor) region of the nifL gene.

In some embodiments, at least one of the deletions and at least one of the promoter insertions are within the central domain (H) of the nifL gene.

In some embodiments, one or more of the deletions are within at least a portion of each of the N-terminal (PAS1 and PAS2 motifs) region, the C-terminal (GHKL nitrogen sensor) region, and the central domain (H) of the nifL gene.

In some embodiments, at least one of the deletions and at least one of the insertions occur at the same location within the bacterium genome.

In some embodiments, the promoter sequence is a copy of a promoter sequence that is native to the wild type diazotrophic γ-proteobacterium (at a different location in the genome). In some such embodiments, the bacterium does not include a trans gene. In some such embodiments, the bacterium does not include an antibiotic resistance marker.

In some embodiments, the bacterium fixes nitrogen by excreting ammonia.

In some embodiments, the bacterium is capable of constitutively synthesizing nitrogenase in the presence of ammonia.

In some embodiments, the relative strength of the inserted promoters is correlated with the extent or rate of ammonia excretion.

In some embodiments, the diazotrophic γ-proteobacterium is of the genus *Klebsiella, Azotobacter* or *Enterobacter*. In some such embodiments, the diazotrophic γ-proteobacterium is of the species *Klebsiella pneumoniae, Azotobacter vinelandii* or *Enterobacter cloacae*. In some such embodiments, the diazotrophic γ-proteobacterium is of the species *Azotobacter vinelandii*.

In a second aspect, the disclosure encompasses a bacterial culture that includes two or more of the genetically modified bacteria described above.

In some embodiments, the culture is capable of excreting ammonia to a concentration of greater than 100 µM. In some such embodiments, the culture is capable of excreting ammonia to a concentration of greater than 500 µM. In some such embodiments, the culture is capable of excreting ammonia to a concentration of greater than 1 mM. In some such embodiments, the culture is capable of excreting ammonia to a concentration of greater than 5 mM. In some such embodiments, the culture is capable of excreting ammonia to a concentration of greater than 8 mM.

In a third aspect, the disclosure encompasses a biofertilizer composition that includes a bacterial culture as described above.

In a fourth aspect, the disclosure encompasses a bacterial/fungal co-culture that includes the bacterial culture described above, along with a fungal culture that includes mycorrhizal fungi.

In some embodiments, the mycorrhizal fungi are of the genus *Laccaria* or *Hebeloma*. In some such embodiments, the mycorrhizal fungi are of the species *Laccaria* bicolor or *Hebeloma cylindrosporum*.

In a fifth aspect, the disclosure encompasses a biofertilizer composition that includes the bacterial/fungal co-culture described above.

In a sixth aspect, the disclosure encompasses an agricultural system that includes either of the biofertilizer compositions described above applied to soil.

In some embodiments, the soil is in contact with a plant or plant seed. In some such embodiments, the plant is a crop plant. In some such embodiments, the crop plant is a cereal grain.

In some embodiments, the plant is a non-leguminous plant.

In a seventh aspect, the disclosure encompasses an agricultural system comprising the either of the biofertilizer compositions described above, in contact with a plant or plant seed.

In some embodiments, the plant is a crop plant. In some such embodiments, the crop plant is a cereal grain.

In some embodiments, the plant is a non-leguminous plant.

In an eighth aspect, the disclosure encompasses a method for making a genetically modified diazotrophic γ-proteobacterium exhibiting an increased ability to fix atmospheric nitrogen. The method includes the steps of (a) deleting one or more portions the nifL gene coding region within a wild type diazotrophic γ-proteobacterium; and (b) inserting within the diazotrophic γ-proteobacterium genome one or more DNA segments that include a promoter sequence. The inserted promoter sequence is placed and oriented to direct transcription of the rnf1 gene complex, which may include one or more of the rnfA1, rnfB1, rnfC1, rnfD1, rnfE1, rnfG1 or rnfH1 genes. By performing these steps, transcription of the rnf1 gene complex is upregulated, resulting in a genetically modified diazotrophic γ-proteobacterium that is capable of fixing nitrogen at a faster rate or to a greater degree than a wild type diazotrophic γ-proteobacterium is produced.

In some embodiments, the promoter or promoters are inserted within the deleted nifL gene region and oriented in the opposite direction of nifL/nifA transcription, thus directing transcription in the upstream direction, away from the nifA gene. This is opposite the direction in which the nifL promoter directs transcription in its "wild type" position in the genome. In such embodiments, the promoter placement and orientation directs transcription towards the rnf1 gene complex (i.e., upstream relative to the nifL gene) and in its normal direction of transcription (i.e., opposite of the direction of transcription of the nifL/nifA genes).

In some embodiments, the bacterium is configured to constitutively synthesize the nitrogenase enzyme, so as to reduce nitrogen to ammonia even in the presence of ammonia in the surrounding environment. In some such embodiments, the upregulation of the expression of the rnf1 gene complex reduces Ferredoxin/Flavodoxin to feed the nitrogenase enzyme.

In some embodiments, at least one of the deleting steps and at least one of the inserting steps are performed within the nifL gene. In some such embodiments, at least one of the deleting steps and at least one of the inserting steps are performed within the N-terminal (PAS1 and PAS2 motifs) region of the nifL gene. In other such embodiments, at least one of the deleting steps and at least one of the inserting steps are performed within the C-terminal (GHKL nitrogen sensor) region of the nifL gene. In yet other such embodiments, at least one of the deleting steps and at least one of the inserting steps are performed within the central domain (H) of the nifL gene.

In some embodiments, at least one of the deleting steps is performed within at least a portion of each of the N-terminal (PAS1 and PAS2 motifs) region, the C-terminal (GHKL nitrogen sensor) region, and the central domain (H) of the nifL gene.

In some embodiments, at least one of the deleting steps and at least one of the inserting steps are performed at the same location within the bacterium genome. In some such embodiments, the deleting step and inserting steps occur simultaneously as a single deletion/insertion step.

In some embodiments, the promoter sequence is a copy of a promoter sequence that is native to the wild type diazotrophic γ-proteobacterium (at a different location in the genome).

In some embodiments, no trans genes are inserted, or if any trans gene is inserted, it is deleted before the genetically modified bacterium is completed.

In some embodiments, no antibiotic resistance markers are inserted, or if any antibiotic resistance marker that is inserted, it is deleted before the genetically modified bacterium is completed.

In some embodiments, the genetically modified bacterium that is made fixes nitrogen by excreting ammonia.

In some embodiments, the genetically modified bacterium that is made is capable of constitutively synthesizing nitrogenase in the presence of ammonia. In some such embodiments, the relative strength of the promoter sequence promoter is correlated with the extent or rate that the genetically modified bacterium excretes ammonia.

In some embodiments, the diazotrophic γ-proteobacterium is of the genus *Klebsiella, Azotobacter* or *Enterobacter*. In some such embodiments, the diazotrophic γ-proteobacterium is of the species *Klebsiella pneumoniae, Azotobacter vinelandii* or *Enterobacter cloacae*. In some such embodiments, the diazotrophic γ-proteobacterium is of the species *Azotobacter vinelandii*.

In a ninth aspect, the disclosure encompasses a method of stimulating plant growth by providing fixed nitrogen to the plant. The method includes the step of applying to the plant, a part of the plant, a seed of the plant, the soil in which the plant is planted, or the soil in which the plant is intended to be planted an effective amount of the biofertilizer composition described above that contains a culture of the genetically modified bacteria. The plant takes up fixed nitrogen produced by the bacterial culture included in the biofertilizer composition, and the plant's growth is effectively stimulated.

In some embodiments, the fixed nitrogen is in the form of excreted ammonia.

In some embodiments, the plant is a crop plant. In some such embodiments, the crop plant is a cereal grain.

In some embodiments, the plant is a non-leguminous plant.

In a tenth aspect, the disclosure encompasses an alternative method of stimulating plant growth by providing fixed nitrogen to the plant. The method includes the step of applying to the plant, a part of the plant, a seed of the plant, the soil in which the plant is planted, or the soil in which the plant is intended to be planted an effective amount of the biofertilizer composition described above that contains a co-culture of the genetically modified bacteria of the genetically modified bacteria and mycorrhizal fungi. The fungal culture included in the biofertilizer composition facilitates the transfer to the plant of the fixed nitrogen produced by the bacterial culture included in the biofertilizer composition, and the plant's growth is effectively stimulated.

In some embodiments, the fixed nitrogen is in the form of excreted ammonia.

In some embodiments, the plant is a crop plant. In some such embodiments, the crop plant is a cereal grain.

In some embodiments, the plant is a non-leguminous plant.

Other features of the disclosed compositions and methods will become apparent from a review of the specification, claims, and drawings.

DETAILED DESCRIPTION

I. In General

Figure 1:
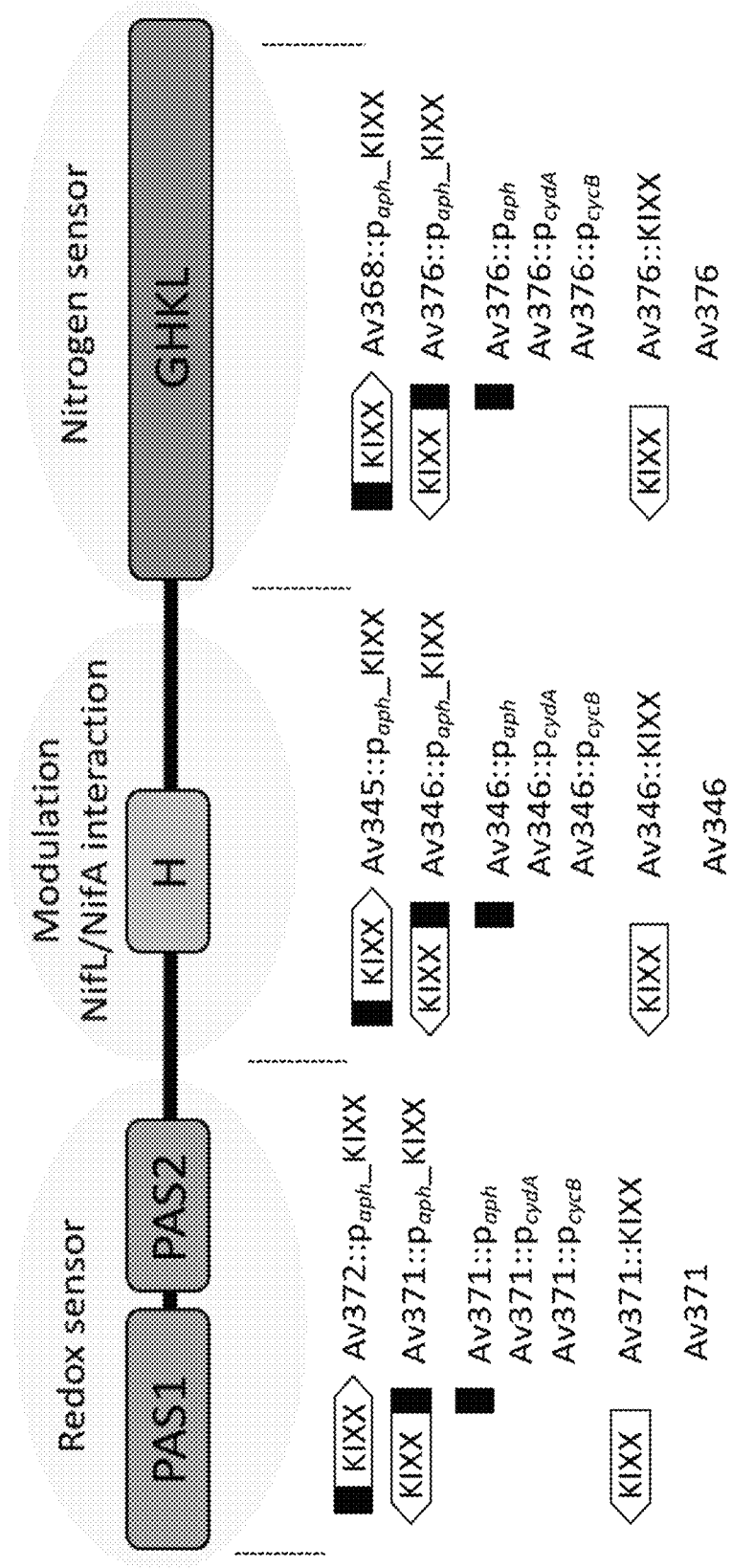
FIG. 1. Cartoon of *A. vinelandii* NifL structure. The numbers refer to the primary amino acid sequence of *A. vinelandii* NifL protein and mark the approximate boundaries of its N-terminal (PAS1 and PAS2 motifs), Central domain (H), and C-terminal domain (GHKL). Map of the nifL region of *A. vinelandii* showing the position of gene deletion insertion. The arrows marked with strain numbers indicate the direction of transcription; KIXX: cassette resistance marker for kanamycin; $p_{-aph}$: aph promoter; $p_{-cydA}$: cydA promoter; $p_{-cycB}$: cycB promoter.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably. The terms "comprising", "including", and "having" can also be used interchangeably.

Unless defined otherwise, all technical and scientific terms used herein have the same meanings as commonly understood by one of ordinary skill in the art.

All publications and patents specifically mentioned herein are incorporated by reference for all purposes including describing and disclosing the chemicals, instruments, statistical analysis and methodologies which are reported in the publications which might be used in connection with the disclosed compositions and methods. All references cited in this specification are to be taken as indicative of the level of skill in the art. Nothing herein is to be construed as an admission that the invention is not entitled to antedate such disclosure by virtue of prior invention.

II. The Invention

We have developed genetically modified diazotrophic γ-proteobacteria that are capable of constitutively synthesizing nitrogenase, resulting in the synthesis of large amounts of fixed nitrogen (in the form of ammonia), even in the presence of ammonia in the surrounding environment. This disclosure includes both the genetically modified bacteria and methods of making the bacteria.

Ammonia, which has the chemical structure $NH_3$, is the basic form of a conjugate acid-base pair that also includes the acidic form ammonium, a cation which has the chemical structure $NH_4^+$. The acidic and basic forms exist together in nature, and can readily interconvert between the two forms. Accordingly, throughout this disclosure, including in the claims, the term "ammonia" encompasses both the basic form $NH_3$, as well its conjugate acid form ammonium, $NH_4^+$.

We have also demonstrated that the genetically modified bacteria are capable of delivering significant amounts of fixed nitrogen to plants, including non-leguminous plants that are not known to form a symbiotic relationship with nitrogen-fixing bacteria, such as, without limitation, cereal grains (e.g., rice, wheat or corn (maize)). Accordingly, this disclosure includes compositions, systems and methods of using cultures of the genetically modified bacteria as biofertilizers to stimulate plant growth and production, while decreasing dependence on chemical nitrogen fertilizers.

The term "non-leguminous plant" refers to plant species that are not classified as legumes. It is well-known in the art as to which plant species are legumes. The term "cereal grain" refers to a grass that is cultivated as a crop for the edible components of its grain (a type of fruit known in the art as a caryopsis).

Finally, we have demonstrated that the genetically modified bacteria are capable of delivering significant amounts of fixed nitrogen to mycorrhizal fungi, which can facilitate the transfer of the fixed nitrogen to plants, including non-leguminous plants that are not known to form a symbiotic relationship with nitrogen-fixing bacteria, such as, without limitation, cereal grains (e.g., rice, wheat or corn (maize)). Accordingly, this disclosure includes compositions, systems and methods of using co-cultures of the genetically modified bacteria and mycorrhizal fungi as biofertilizers to increase plant growth and production, while decreasing dependence on chemical nitrogen fertilizers.

A. Genetically Modified Bacteria

We have developed genetically modified ammonia excreting strains of Azotobacter vinelandii, a diazotrophic γ-proteobacterium. The genetically modified strains constitutively synthesize nitrogenase, and thus synthesize and excrete substantial amounts of fixed nitrogen in the form of ammonia, even in the presence of ammonia in the external environment.

Azotobacter vinelandii was chosen as the exemplary diazotrophic γ-proteobacterium for our proof of concept, because it is known to fix nitrogen even in ambient oxygen environments, while most other diazotrophs require low oxygen environments to fix nitrogen.

The ammonia excreting strains were genetically modified in two ways. At least a portion of the nifL gene was deleted, and a DNA segment containing a promoter sequence was inserted within the nifL gene, in an orientation directing transcription in the upstream direction (in the opposite direction in which transcription of the gene normally occurs).

Figure 11:
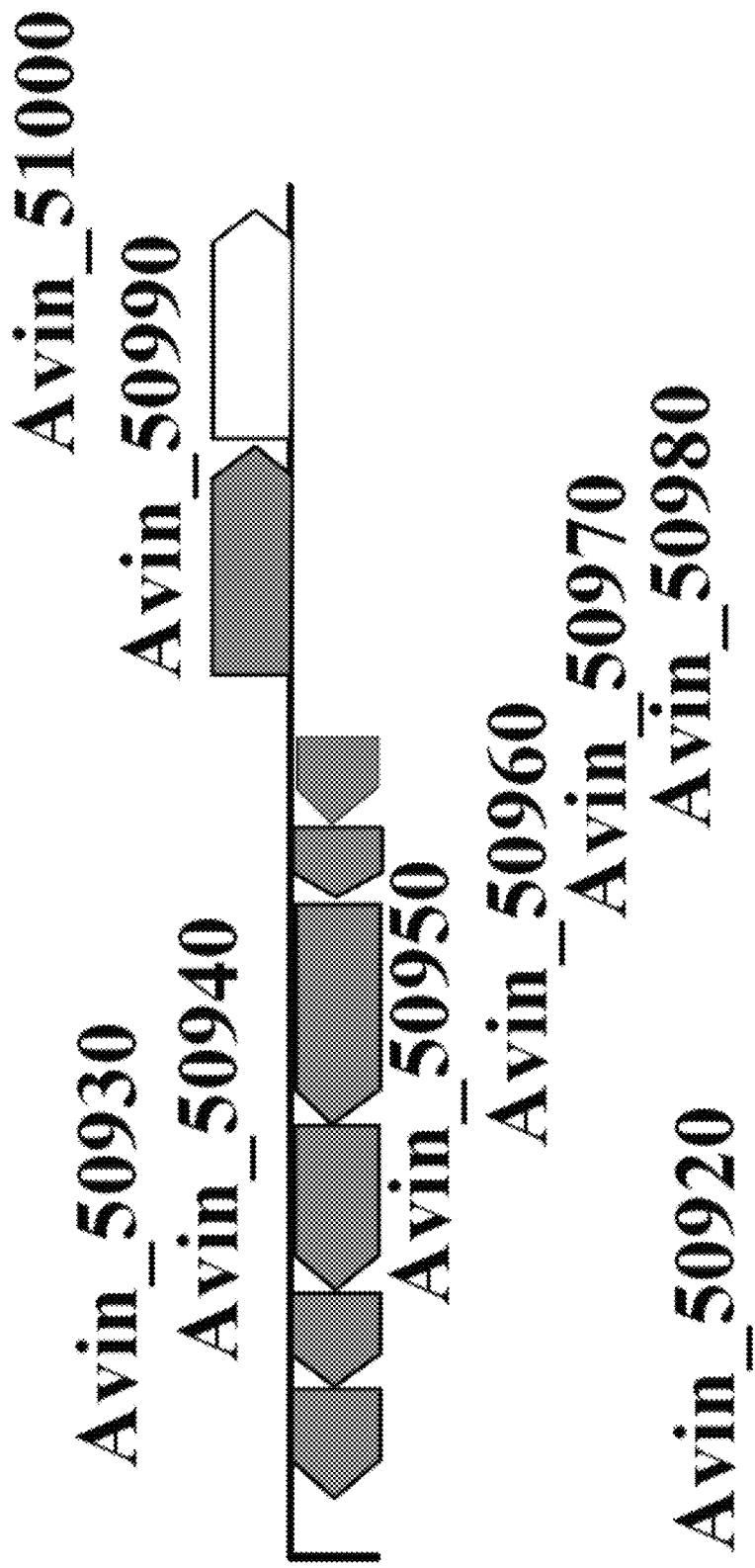
FIG. 11. A graphic showing gene organization and direction of transcription for relevant genes in A. vinelandii DJ strain. Avin_50920: rnfH1, Avin_50930: rnfE1, Avin_50940: rnfG1, Avin_50950: rnfD1, Avin_5060: rnfC1, Avin_50970: rnfB1, Avin_50980: rnfA1, Avin_50990: nifL, Avin_51000: nifLA. As seen in the FIG. 11, the rnf1 gene complex in A. vinelandii DJ strain is situated upstream of the nifL gene and has the opposite direction of transcription. Accordingly, a promoter inserted into the nifL gene region and oriented to direct transcription in the opposite direction of the nifL gene is configured to direct transcription (and upregulate expression) of the rnf1 gene complex.

By inserting the promoter into the nifL gene region in this orientation, the promoter is placed and oriented to direct the transcription of (and thus upregulate the expression of) one or more genes in the rnf1 gene complex, which is upstream from and transcribed in the opposite direction of the nifL gene (see FIG. 11). The upregulated expression of the rnf1 gene complex acts to supply reduced Ferrodoxin/Flavodoxin, which feeds the constitutively synthesized nitrogenase enzyme with low potential electrons, thus ensuring efficient nitrogen fixation.

As the skilled artisan would recognize, other diazotrophic γ-proteobacterium species or strains may have different arrangements and/or orientations for the relevant genes (nifL/nifA and rnf1). So the placement and orientation of the inserted promoter may not be the same in all diazotrophic γ-proteobacterium species or strains as it we report here for the exemplary *Azotobacter vinelandii*. Instead, the promoter is inserted into the bacterial genome in any location and orientation that would direct transcription of the rnf1 gene complex within the given diazotrophic γ-proteobacterium species or strain that is being modified.

Notably, the extent of ammonia excretion was correlated with the known strength of the promoter of the inserted promoter sequence. Accordingly, the amount and\or rate of ammonia excretion can be controlled by choosing a promoter sequence for insertion based on the known strengths of potential promoters. In this way, the genetically modified strains can be "tuned" to the amount of ammonia excretion that is appropriate for use with specific crops and/or environmental conditions.

Given the environmental and regulatory issues raised by introducing into the environment organisms having trans genes, we have developed exemplary genetically modified bacteria that do not include any trans genes. In such strains, the inserted promoters are copies of promoter sequences that occur elsewhere within the wild type genome.

The disclosed genetically modified bacteria having an ammonia excreting phenotype can be supported by a variety of different carbon sources. In certain embodiments, the genetically modified bacteria may further be genetically modified to be adapted to a specific carbon source, such as to a specific target crop. Such further modifications would help control the undesirable spread of the bacteria beyond the target crop, such into streams and rivers.

The genetically modified strains excrete substantially more ammonia than has been previously reported for any other genetically modified diazotrophic γ-proteobacterium. Accordingly, they can be used in safe and effective biofertilizers for providing fixed nitrogen to plants. Further details are provided below.

B. Methods of Making the Genetically Modified Bacteria

Methods of making the genetically modified from wild type bacterium include any methods known in the art for accomplishing the required deletion and/or insertion. In some embodiments, the deletion and insertion occur in a single step.

In a non-limiting example, the modifications may be accomplished in one or more steps via the design and construction of appropriate vectors and transformation of the host cell with those vectors. Nucleic acid constructs used in the methods may be prepared in conventional ways, by isolating the desired genes from an appropriate host, by synthesizing all or a portion of the genes, or combinations thereof. Similarly, the promoter sequences, the regulatory signals, the transcriptional and any required translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

Targeted integration can be accomplished by designing a vector having regions that are homologous to the upstream (5'-) and downstream (3'-) flanks of the target gene. Either of both of these regions may include a portion of the coding region of the target gene. A gene cassette (including associated promoters and terminators if different from those of the target gene) and selection markers (with associated promoters and terminators as may be needed) can optionally reside on a vector between the regions that are homologous to the upstream and downstream flanks of the target gene. Targeted cassette insertion can be verified by any appropriate method, such as, for example, PCR.

C. Using the Genetically Modified Bacteria to Provide Fixed Nitrogen and Thus Stimulate Growth in Plants Cereals like corn (*Zea mays*) and rice (*Oryza sativa*) require large amounts of nitrogen to reach good yields. Unfortunately, these crop plants are not able to associate with *rhizobia* or more generally with nitrogen-fixing bacteria, and therefore require large amounts of nitrogen inputs, generally in the form of chemical nitrogen fertilizers. Currently, there is no efficient technology demonstrated to deliver significant amounts of fixed nitrogen to cereal crops.

Using $^{15}N_2$ gas enrichment experiments, we have shown that inoculation of rice (and pine trees) with an ammonia excreting nifL mutant of *A. vinelandii* (as described above) led to a very significant $^{15}N$ enrichment, as compared to rice (and pine trees) inoculated with the non-fixing (nifD) mutant, indicating that the nifL mutation in *A. vinelandii* allows rice (and pine trees) to obtain large amounts of nitrogen from the atmosphere. This provides proof of concept for using the genetically modified bacteria to transfer significant amounts of fixed nitrogen to a major cereal crop.

Accordingly, the disclosure further includes inoculums comprising the genetically modified bacteria that can be applied to plants, plant seeds, or the soil in which the plant is planted or will be planted.

In a non-limiting example, such a bacterial inoculum can comprise a genetically modified bacterium and a culture medium. In some embodiments, the genetically modified bacterium is *A. vinelandii*. In some embodiments, the culture medium is a liquid culture medium. Bacterial inocula include large-scale preparations of sufficient quantities of viable genetically modified bacterial cells for use in, for example, biofertilizers and other commercial agricultural applications.

When used in biofertilizers, the genetically modified bacteria may stimulate plant growth by providing a source of bioavailable nitrogen to plants. "Stimulated" plant growth means that the quantity, weight and/or size of one or more parts of the plant is increased, relative to a plant where the seed, seedling, plant, or plant part has not been contacted with the biofertilizer. Such increased quantity, size or mass may include, but is not limited to, increased length of the root system, increased number of crown roots, increased number of lateral roots, increased dry weight, increased shoot length, or some combination of these. Such plant growth stimulation can have some beneficial effects on the plant, including, without limitation, enhancing soil nutrient acquisition, facilitating the establishment of young plants in the field, and increasing crop plant yield.

In some embodiments, the biofertilizer is applied to a non-leguminous plant, non-leguminous plant seed, or to the soil in which a non-leguminous plant is planted or will be planted. In some such embodiment, the non-leguminous plant is a monocotyledon. In some such embodiments, the monocotyledon is a cereal grain. Non-limiting examples of cereal grains that can be used with the method include rice, wheat and corn (maize).

D. Using Co-Cultures of the Genetically Modified Bacteria and Mycorrhizal Fungi to Provide Fixed Nitrogen and Thus Promote Growth in Plants Interactions with arbuscular mycorrhizal fungi are widespread in land plants, and this association aids in the uptake of nutrients from the soil. However, it has never been shown that mycorrhizal fungi can acquire nitrogen from nitrogen fixing bacteria. We have developed "mixed inoculants" of mycorrhizal fungi and the genetically modified bacteria described above, where the mycorrhizal fungi serve as "adaptors" between the plant and the nitrogen-fixing bacteria.

In proof of concept experiments using $^{15}N_2$ gas enrichment, we have shown that two mycorrhizal fungi (*Laccaria bicolor* and *Hebeloma cylindrosporum*) can acquire nitrogen from the air through *A. vinelandii* nifL mutants. This result suggests that a co-culture of the genetically modified bacteria and mycorrhizal fungi may be used transfer significant amounts of fixed nitrogen to a crop plant.

In related experiments, we have demonstrated that mycorrhizal fungi can be used in combination with the engineered bacteria to facilitate nitrogen fixation in corn plants.

Accordingly, the disclosure further includes inoculums comprising the genetically modified bacteria and mycorrhizal fungi that can be applied to plants, plant seeds, or the soil in which the plant is planted or will be planted.

In a non-limiting example, such a mixed inoculum can comprise a genetically modified bacterium, a mycorrhizal fungus and a culture medium. In some embodiments, the genetically modified bacterium is *A. vinelandii*. In some embodiments, the culture medium is a liquid culture medium. Mixed inocula include large-scale preparations of sufficient quantities of viable genetically modified bacterial cells and mycorrhizal fungi cells for use in, for example, biofertilizers and other commercial agricultural applications.

When used in biofertilizer, a co-culture or mixed inoculant of the genetically modified bacteria and mycorrhizal fungi may stimulate plant growth by providing a source of bioavailable nitrogen to plants.

In some embodiments, the biofertilizer is applied to a non-leguminous plant, non-leguminous plant seed, or to the soil in which a non-leguminous plant is planted or will be planted. In some such embodiment, the non-leguminous plant is a monocotyledon. In some such embodiments, the monocotyledon is a cereal grain. Non-limiting examples of cereal grains that can be used with the method include rice, wheat and corn (maize).

The specific features and advantages of the present invention will become more apparent after a review of the following experimental examples. However, the invention is not limited to the specific embodiments disclosed herein.

III. Examples

The following Examples are offered by way of illustration only, and not by way of limitation.

Example 1: Construction *Azotobacter vinelandii* nifL Chromosomal Mutants and Screening of Mutants for Ammonia Excretion In this example, we show that certain genetically modified nifL mutants of *A. vinelandii* synthesize nitrogenase constitutively in the presence of ammonia and, unexpectedly, excrete large amounts of ammonia during nitrogen fixation. Up to 10 mM ammonia were found in the culture medium toward the end of the exponential growth phase. The large amounts of ammonia excreted by *A. vinelandii* nifL mutants have not been reported in other diazotrophic bacteria where nifL gene has been identified.

Notably, we have engineered through gene editing ammonia excreting strains of *A. vinelandii* that lack any trans genes. Furthermore, the amounts of ammonia excreted can be controlled and regulated. The ability to modulate the amounts of ammonia excreted constitutes a unique feature to match the specific fixed nitrogen requirements for each crop's targeted cultivars.

Introduction and Background

*Azotobacter vinelandii* is a free-living nitrogen-fixing (diazotrophic) bacterium of the gamma-proteobacteria. It is found in soils worldwide, and it able to adapt its metabolism to diverse sources of nutrients. In diazotrophic gamma proteobacteria, such as *A. vinelandii* and *K. pneumoniae*, NifL and NifA work in concert to sense environmental factors (NifL) and conditionally activate expression (NifA) of nitrogen fixation genes (nif genes).

In these exemplary γ-proteobacteria, NifL inhibits NifA activity in response to environmental changes, so as to tightly control nitrogen fixation and avoid the unnecessary consumption of energy. The inhibition of NifA activity by NifL occurs via direct protein-protein interaction and complex formation between NifL and NifA.

In *A. vinelandii*, NifA must bind upstream of the promoters of all nif operons for enabling their expression. NifL is a modular protein in which each subunit is composed of three linked domains: two N-terminal Per-ARNT-Sim (PAS) domains are connected by a Q-linker region (H domain) to a C-terminal domain whose sequence is homologous to the histidine kinases of bacterial two-component signaling systems. The N-terminal, FAD-containing, PAS domain of *A. vinelandii* is responsible for the redox-mediated regulation of the NifA.

The C-terminal kinase-like domain of NifL is required for binding of NifL to the activator NifA. Although there is significant sequence homology between kinase effector domains of bacterial two-component systems and the C-terminal domain of NifL, signal transduction between NifL and NifA is transmitted directly through protein-protein interactions and not via phosphorylation.

The central domain of NifL has been found to be involved in bringing about the change in the conformation of NifL that dictates whether NifL would be active or inactive in blocking NifA function in response to the status of fixed nitrogen or oxygen. In the absence of oxygen, the FAD of NifL is reduced and NifA is free to activate transcription of nif genes. Upon oxidation of the FAD, NifL acts as an anti-activator and binds to NifA to prevent activation of nif gene expression.

Adjacent to nifL/nifA (gene identification number for *A. vinelandii* DJ strain: Avin_50990, Avin_51000) genes cluster is the rnf1 region (upstream). Three additional genes are part of this transcriptional unit: Avin_50890 (conserved hypothetical protein), Avin_50900 (nitrogen fixation-related protein), and Avin_50910 (nafY).

Exemplary *A. vinelandii* Mutations and Resulting Phenotypes

In Vivo Insertion/Deletion Mutations of nifL Gene in the Chromosome of *A. vinelandii*, Thereby Removing Different Domains of the Native NifL Protein, Result in Different Phenotypes.

Different mutations of the nifL gene in *A. vinelandii* have been achieved using insertion-deletion strategy. In frame deletions of the 1) entire coding region, 2) the region encoding the N-terminal domain, 3) the region encoding just the central domain, and 4) the region encoding C-terminal domain, have been achieved by gene replacement approach with the insertion of the kanamycin resistance (KIXX) gene from transposon Tn5 isolated from the PUC4-KIXX vector (Prentki P and Krisch H M, 1984) under the control of the aph promoter (promoter of the aminoglycoside phosphotransferase gene from the neomycin producer *Streptomyces fradiae*), or by congression approach (coincidental transfer of genetic markers using rifampin (Rif$^R$) and kanamycin (Kan$^R$) resistance as the selection marker as previously described by Jacobson et al., 1989) to insert the KIXX cassette lacking the aph promoter sequence into the chromosome or to remove KIXX cassette and aph promoter from the chromosome (FIG. 1).

In frame deletions of the 5) the regions encoding the N-terminal, central and C-terminal domains have been achieved by the insertion of the aph (promoter from kanamycin resistance gene), cydA (promoter from *A. vinelandii* cydA gene; Avin_19890), or cycB (promoter from *A. vinelandii* cydB gene; Avin_47940) promoter region sequences (FIG. 1).

1) Deletion of the entire nifL gene has been achieved by insertion of the KIXX cassette allowing the aph promoter within KIXX cassette to direct the transcription from KIXX away from nifLA. This deletion resulted in a strain (ΔnifL: p$_{aph}$_KIXX) with a Nif minus phenotype who does not excrete ammonia.

2) Chromosomal mutants with a deletion of nifL removing the region encoding the N-terminal domain of the native protein NifL have been generated by insertion of the KIXX cassette in both orientations, allowing the aph promoter within KIXX cassette to direct the transcription from KIXX away from nifLA or in the same direction as nifLA. Strain bearing a deletion of the N-terminal domain with insertion of the KIXX cassette allowing the aph promoter within KIXX cassette to direct the transcription from KIXX in the same direction as nifLA (AvFM372::p$_{aph}$_KIXX) could not be isolated free of wild-type nifL, suggesting that such deletion could be lethal for *A. vinelandii*, while the deletion of N-terminal of NifL with the insertion the KIXX cassette allowing the aph promoter within KIXX cassette to direct the transcription from KIXX away from nifLA (AvFM371:: p$_{aph}$_KIXX) resulted in a strain with a Nif plus phenotype who excretes large amounts of ammonium ion within 48 hours (up to 12 mM).

Deletion of the N-terminal domain achieved through congression (coincidental transfer of genetic markers using rifampin (Rif$^R$) and kanamycin (Kan$^R$) resistance as the selection marker as previously described by Jacobson et al., 1989) using the AvFM371::p$_{aph}$_KIXX strain, and by the insertion of the KIXX cassette lacking the aph promoter sequence in the opposite orientation as nifLA transcription resulted in strain (Av371::KIXX) with a Nif plus phenotype who does not excrete ammonia.

Similar deletion has been achieved through congression (coincidental transfer of genetic markers using rifampin (Rif$^R$) and kanamycin (Kan$^R$) resistance as the selection marker as previously described by Jacobson et al., 1989) to remove the KIXX cassette and aph promoter from the chromosome of the AvFM371::p$_{aph}$_KIXX strain, resulting in the absence of a trans gene. This deletion (Δ371) resulted in strain with a Nif plus phenotype who does not excrete ammonia.

3) Chromosomal mutants with a deletion of nifL removing the central domain of the native protein NifL have been generated by insertion of the KIXX cassette in both orientations, allowing the aph promoter within KIXX cassette to direct the transcription from KIXX away from nifLA or in the same direction as nifLA. Strain bearing a deletion of the N-terminal domain with insertion of the KIXX cassette allowing the aph promoter within KIXX cassette to direct the transcription from KIXX in the same direction as nifLA (AvFM345::p$_{aph}$_KIXX) could not be isolated free of wild-type nifL, suggesting that such deletion could be lethal for *A. vinelandii*, while the deletion of central domain of NifL with the insertion the KIXX cassette allowing the aph promoter within KIXX cassette to direct the transcription from KIXX away from nifLA (AvFM346::p$_{aph}$_KIXX) resulted in a strain with a Nif plus phenotype who excretes up to 6 mM ammonia at 48 hours' time point.

Deletion of the central domain achieved through congression (coincidental transfer of genetic markers using rifampin (Rif$^R$) and kanamycin (Kan$^R$) resistance as the selection marker as previously described by Jacobson et al., 1989) using the AvFM346::p$_{aph}$_KIXX strain, and by the insertion of the KIXX cassette lacking the aph promoter sequence in the opposite orientation as nifLA transcription resulted in strain (Av346::KIXX) with a Nif plus phenotype who does not excrete ammonia.

Similar deletion has been achieved through congression (coincidental transfer of genetic markers using rifampin (Rif$^R$) and kanamycin (Kan$^R$) resistance as the selection marker as previously described by Jacobson et al., 1989) to remove the KIXX cassette and aph promoter from the chromosome of the AvFM346::p$_{aph}$_KIXX strain, resulting in the absence of a trans gene. This deletion (Δ346) resulted in strain with a Nif plus phenotype who does not excrete ammonia.

4) Chromosomal mutants with a deletion of nifL removing the region encoding the C-terminal of the native protein NifL have been generated by insertion by insertion of the KIXX cassette in both orientations, allowing the aph promoter within KIXX cassette to direct the transcription from KIXX away from nifLA or in the same direction as nifLA. Strain bearing a deletion of the C-terminal domain with insertion of the KIXX cassette allowing the aph promoter within KIXX cassette to direct the transcription from KIXX in the same direction as nifLA (AvFM368::p$_{aph}$_KIXX) could not be isolated free of wild-type nifL, suggesting that such deletion could be lethal for *A. vinelandii*, while the deletion of C-terminal of NifL with the insertion the KIXX cassette allowing the aph promoter within KIXX cassette to direct the transcription from KIXX away from nifLA (AvFM376::p$_{aph}$_KIXX) resulted in a strain with a Nif plus phenotype who excretes large amounts of ammonium ion within 48 hours (up to 10 mM).

Deletion of the C-terminal domain achieved through congression (coincidental transfer of genetic markers using rifampin (Rif$^R$) and kanamycin (Kan$^R$) resistance as the selection marker as previously described by Jacobson et al., 1989) using the AvFM376::p$_{aph}$_KIXX strain, and by the insertion of the KIXX cassette lacking the aph promoter sequence in the opposite orientation as nifLA transcription resulted in strain (Av376::KIXX) with a Nif plus phenotype who does not excrete ammonia.

Similar deletion has been achieved through congression (coincidental transfer of genetic markers using rifampin (Rif$^R$) and kanamycin (Kan$^R$) resistance as the selection marker as previously described by Jacobson et al., 1989) to remove the KIXX cassette and aph promoter from the chromosome of the AvFM376::p$_{aph}$_KIXX strain, resulting in the absence of a trans gene. This deletion (Δ376) resulted in strain with a Nif plus phenotype who does not excrete ammonia.

Discussion

Figure 2:
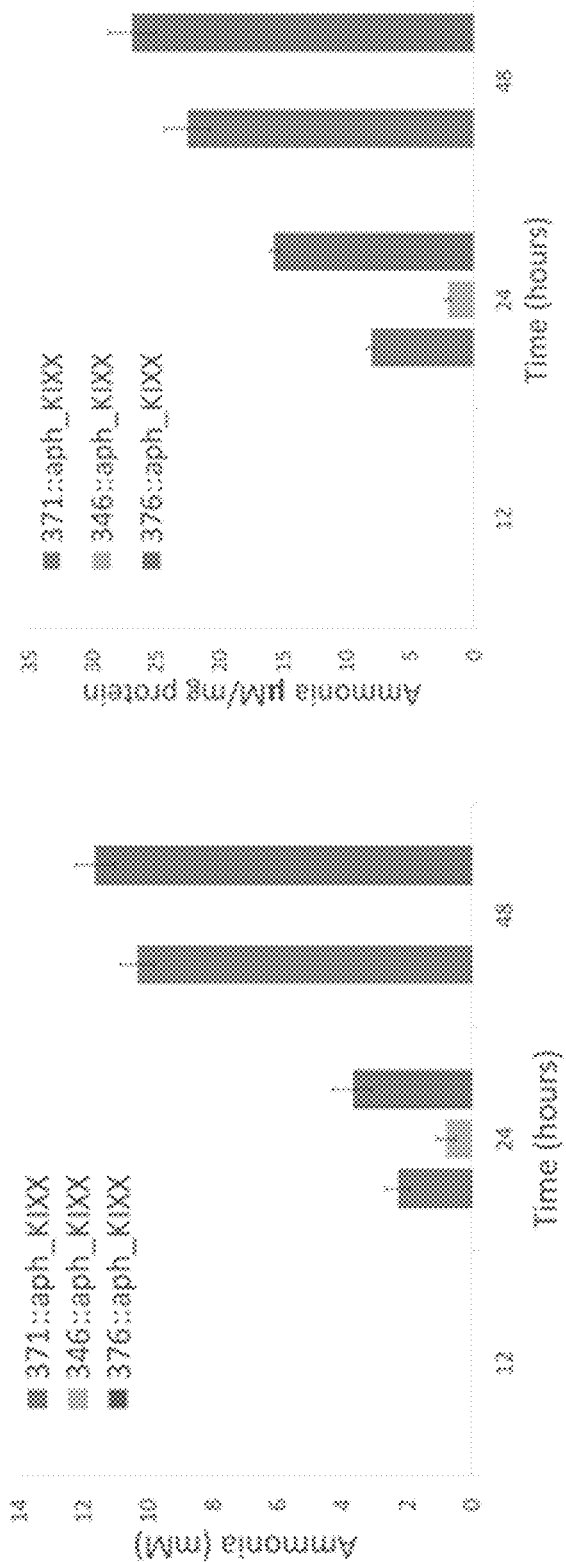
FIG. 2. Ammonium excretion quantification in the medium and ammonia excretion quantification correlated to total amount of protein. AvFM371::$p_{aph}$_KIXX: 371::aph_KIXX, AvFM346::$p_{aph}$_KIXX: 346::aph_KIXX, AvFM376::$p_{aph}$_KIXX: 376::aph_KIXX.

First Conclusion: The different nifL mutant strains described above presented different phenotypes: lethal phenotype, Nif minus phenotype (strain not capable of growing on N$_2$), Nif plus phenotype (strain capable of growing on N$_2$), and Nif plus phenotype associated with ammonia excretion phenotype. Only the deletions of N-terminal or C-terminal domain of NifL with the insertion of the KIXX cassette allowing the aph promoter within KIXX cassette to direct the transcription from KIXX away from nifLA (AvFM371::p$_{aph}$_KIXX; AvFM376::p$_{aph}$_KIXX) resulted in strains with a Nif plus phenotype who excrete large amounts of ammonia ion within 48 hours (up to 12 mM) (FIG. 2). The deletion of the central domain, however, with the insertion of the KIXX cassette allowing the aph promoter within KIXX cassette to direct the transcription from KIXX away from nifLA (nifLA (AvFM346::p$_{aph}$_KIXX) resulted in a strain with a Nif plus phenotype who excrete small amount of ammonia within 48 hours (up to 6 mM) (FIG. 2).

Deletion of the N- and C-terminal domains achieved through congression (coincidental transfer of genetic markers using rifampin (Rif$^R$) and kanamycin (Kan$^R$) resistance as the selection marker as previously described by Jacobson et al., 1989) using the AvFM371::p$_{aph}$_KIXX/AvFM376::p$_{aph}$_KIXX strain, and by the insertion of the aph (promoter from kanamycin resistance gene), and cydA (promoter from A. vinelandii cydA gene; Avin_19890) promoter region sequences in the opposite orientation than nifLA transcription (AvFM371::p$_{aph}$; AvFM371::p$_{cydA}$; AvFM376::p$_{aph}$; AvFM376::p$_{cydA}$) resulted in strains with a Nif plus phenotype who excrete large amounts of ammonium ion within 48 hours (up to 12 mM).

Deletion of the N-terminal domain achieved through congression (coincidental transfer of genetic markers using rifampin (Rif$^R$) and kanamycin (Kan$^R$) resistance as the selection marker as previously described by Jacobson et al., 1989) using the AvFM376::p$_{aph}$_KIXX strain, and by the insertion of the or cycB (promoter from A. vinelandii cydB gene; Avin_47940) promoter region sequence in the opposite orientation than nifLA transcription (AvFM376::p$_{cycB}$) resulted in a strain with a Nif plus phenotype who does not excrete ammonia.

Figure 3:
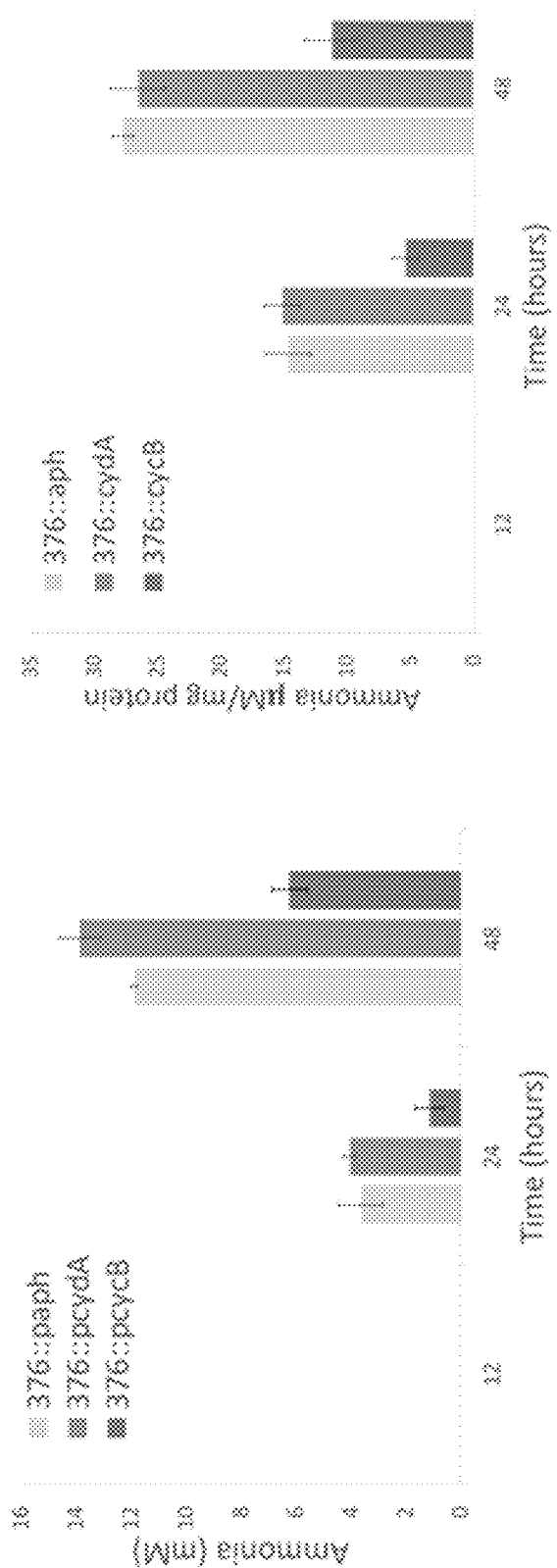
FIG. 3. Ammonium excretion quantification in the medium and ammonia excretion quantification correlated to total amount of protein. AvFM376::$p_{aph}$: 376::paph, AvFM376::$p_{cydA}$: 376::pcydA, AvFM376::$p_{cycB}$: 376::pcycB.
Figure 4:
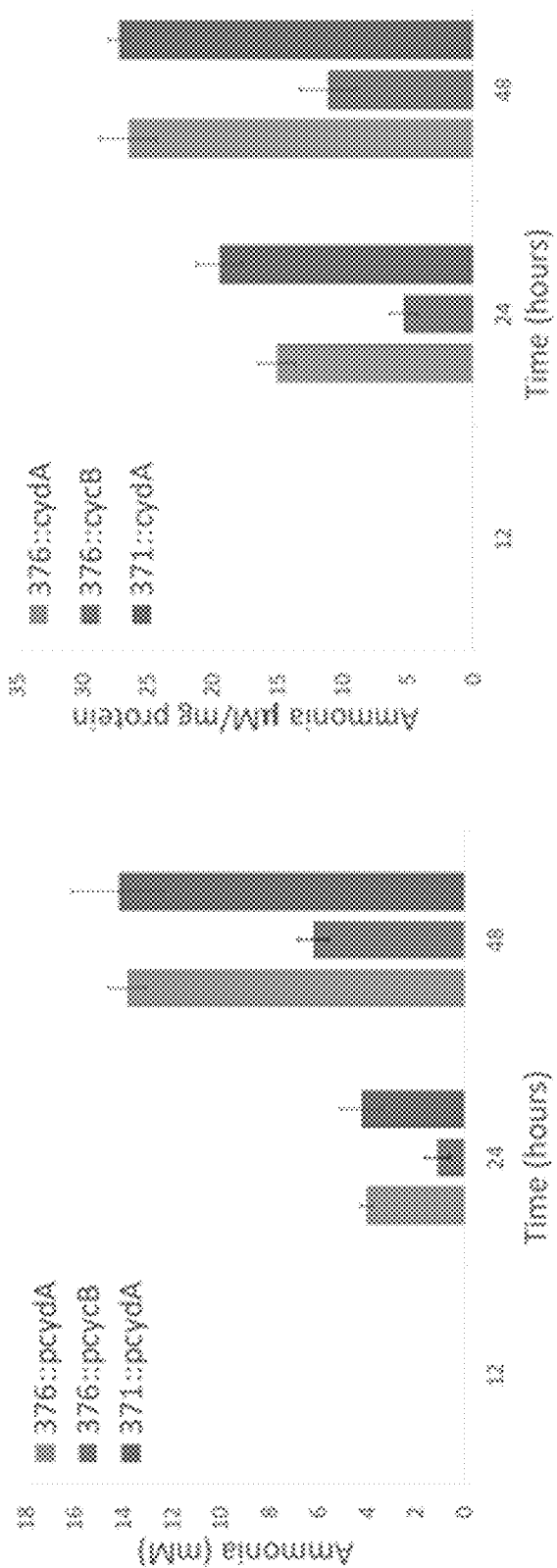
FIG. 4. Ammonium excretion quantification in the medium and ammonia excretion quantification correlated to total amount of protein. AvFM376::$p_{cydA}$: 376::pcydA, AvFM376::$p_{cycB}$: 376::pcycB, AvFM371::$p_{cydA}$: 371::pcydA.

Deletion of the C-terminal domain achieved through congression (coincidental transfer of genetic markers using rifampin (Rif$^R$) and kanamycin (Kan$^R$) resistance as the selection marker as previously described by Jacobson et al., 1989) using the AvFM376::p$_{aph}$_KIXX strain, and by the insertion of the or cycB (promoter from A. vinelandii cydB gene; Avin_47940) promoter region sequence in the opposite orientation than nifLA transcription (AvFM376::p$_{cycB}$) resulted in a strain with a Nif plus phenotype who excretes half of the amounts of ammonia detected for AvFM376::p$_{aph}$ and AvFM376::p$_{cydA}$ strains (up to 6 mM) (FIGS. 3 and 4).

Second Conclusion: Promoter region sequences inserted in the opposite orientation than nifLA transcription and removing the N- and C-terminal domains of NifL are responsible for the Nif plus phenotype associated with large amounts of ammonia excretion phenotype. The amounts of ammonia produced can be modulated by using different promoter sequences. However, the amounts of ammonia released in the growth medium are not directly proportionally correlated with the promoter strength. Therefore, tight regulation of upstream genes from nifLA operon could possibly be required and essential for optimal ammonia excretion.

TABLE 1

List of the nifL mutant strains generated in this example.

| Strain | Deletion | Marker | Phenotype |
| --- | --- | --- | --- |
| ΔnifL::p$_{aph}$_KIXX | deletion of whole nifL gene | p$_{aph}$_KIXX | Nif$^-$ |
| Av371::p$_{aph}$_KIXX | deletion of N-terminal domain | p$_{aph}$_KIXX | Nif$^+$ + ammonium ion excretion |
| Av372::p$_{aph}$_KIXX | deletion of N-terminal domain | p$_{aph}$_KIXX | lethal |
| Av371 | deletion of N-terminal domain | — | Nif$^+$ |
| Av346::p$_{aph}$_KIXX | deletion of Central domain | p$_{aph}$_KIXX | Nif$^+$ |
| Av345::p$_{aph}$_KIXX | deletion of Central domain | p$_{aph}$_KIXX | lethal |
| Av346 | deletion of Central domain | — | Nif$^+$ |
| Av376::p$_{aph}$_KIXX | deletion of C-terminal domain | p$_{aph}$_KIXX | Nif$^+$ + ammonium ion excretion |
| Av368::p$_{aph}$_KIXX | deletion of C-terminal domain | p$_{aph}$_KIXX | lethal |
| Av371 | deletion of C-terminal domain | — | Nif$^+$ |
| Av376::KIXX | deletion of C-terminal domain | KIXX | Nif$^+$ |
| Av376::p$_{aph}$ | deletion of C-terminal domain | p$_{aph}$ | Nif$^+$ + ammonium ion excretion |
| Av376::p$_{cydA}$ | deletion of C-terminal domain | p$_{cydA}$ | Nif$^+$ + ammonium ion excretion |

TABLE 1-continued

List of the nifL mutant strains generated in this example.

| Strain | Deletion | Marker | Phenotype |
|---|---|---|---|
| Av376::$p_{cycB}$ | deletion of C-terminal domain | $p_{cycB}$ | Nif⁺ + ammonium ion excretion |
| Av371-376::$p_{aph}$_KIXX | deletion of N-terminal, central, and C-terminal domains | $P_{aph}$_KIXX | Nif⁺ + ammonium ion excretion |

In addition to the mutants reported in Table 1 above, we have also constructed a new nifL mutant strain using methods similar to those outlined below that combines deletion of the N-terminal domain, the central domain, and the C-terminal domain. This mutant also exhibits the Nif plus phenotype and excretes ammonia.

More specifically, chromosomal mutant with a deletion of nifL removing the N-terminal, central, C-terminal domains of the native protein NifL has been generated by insertion of the KIXX cassette allowing the aph promoter within KIXX cassette to direct the transcription from KIXX away from nifLA. The combined deletion of N-terminal, central, C-terminal domains of NifL with the insertion the KIXX cassette allowing the aph promoter within KIXX cassette to direct the transcription from KIXX away from nifLA (AvFM371-376::$p_{aph}$_KIXX) resulted in a strain with a Nif plus phenotype who excretes up to 12 mM ammonium ion at the time point 48 hours.

In summary, we found that only certain nifL mutants of *A. vinelandii* synthesize nitrogenase constitutively in the presence of ammonium, and unexpectedly excrete large amounts of ammonium during nitrogen fixation. Up to 12 mM ammonium were found in the culture toward the end of the exponential growth phase, contrasting with the nifL mutants of *K. pneumoniae* reported to excrete less than 100 μM ammonium (Bali et al., 1992). The unique property of these ammonium excreting strains in *A. vinelandii* can be used in to enhance and sustain biological nitrogen fixation in agricultural systems.

Materials and Methods

Figure 5:
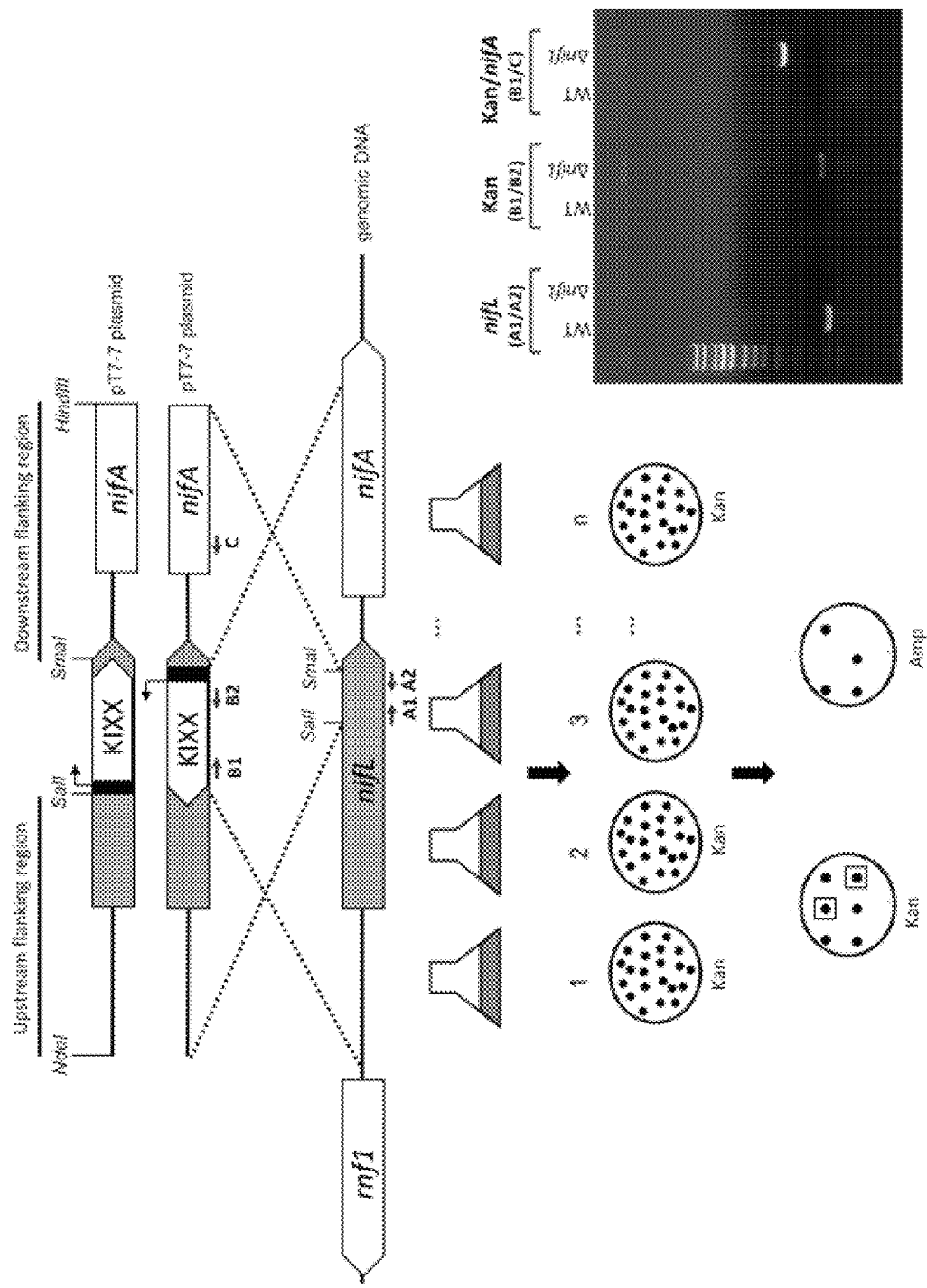
FIG. 5. Construction of chromosomal AvFM376::$p_{aph}$-KIXX nifL mutant strategy.

1. Construction of Chromosomal nifL Mutants in *Azotobacter vinelandii* (FIG. 5)

A. Deletion of the GHKL Domain of NifL:

Av376::$p_{aph}$_KIXX/Av368::$p_{aph}$_KIXX/376 strains.

Construction of the AvFM376::$p_{aph}$_KIXX and AvFM368::$p_{aph}$_KIXX strains—The Av376::$p_{aph}$_KIXX nifL and the Av368::$p_{aph}$_KIXX nifL mutant strains were obtained by gene disruption with an insertion of an antibiotic resistance cassette KIXX between the SalI and SmaI sites, thereby removing the C-terminal quarter of the native NifL sequence. DNA fragment containing the 1276 bp upstream and 1306 bp downstream genomic regions of the nifL (see supplemental material) bearing the SalI (GTCGAC) and SmaI (CCCGGG) restriction sites were obtained by PCR, using genomic DNA from *A. vinelandii* strain DJ. Specific primers nifL376-upstream-F-NdeI and nifL376-downstream-R-HindIII (see Table 2) were used for the amplification of a 2798 bp fragment.

TABLE 2

List of the Primers

| Name | Sequence | Tm |
|---|---|---|
| nifL376-upstream-F-NdeI | 5'-GGAATTCCATATGCGATTAAGGTGC GGCACAGGATTTGCTAATCTTCTCT-3' (SEQ ID NO: 1) | 67.3° C. |
| nifL376-downstream-R-HindIII | 5'-CCCAAGCTTAACTTGCCCTTTTCCA CCTCGCTTTCCAGGT-3' (SEQ ID NO: 2) | 69° C. |
| pKan-F-SmaI | 5'-CCCGGATCCGTCGAGCTCCCGGGAA GCTTCTCG-3' (SEQ ID NO: 3) | 71.8° C. |
| pKan-R-SalI | 5'-TGCGGTCGACGCGAAACGATCCTCA TCCTGTCTCTTGATCAGATCTTGATCC C-3' (SEQ ID NO: 4) | 70.4° C. |
| $p_{cydA}$-F-SmaI | 5'-CCGGAATTCCTGCAGGTAGCCGAAC ACCTCCAGGTCCCGCCTTCC-3' (SEQ ID NO: 5) | 73.2° C. |
| $p_{cydA}$-R-SalI | 5'-TCCCCCGGGACTCCGGCGCATTTCT AGCGGCCGCCGAAGTTCT-3' (SEQ ID NO: 6) | 76.2° C. |
| $p_{cycB}$-F-SmaI | 5'- GCCGACGTCGACCGTGGCTGATTA CGTGCGCCCGCGGC-3' (SEQ ID NO: 7) | 76.2° C. |
| $p_{cycB}$-R-SalI | 5'-GCCGACGTCGACCGTGGCTGATTAC GTGCGCCCGCGGC-3' (SEQ ID NO: 8) | 76.2° C. |
| nifL376-downstream-F-EcoRI | 5'- GGGGAATTCCATTCCGCCCGACCT GGTGCTGAAGGTGTTCGA-3' (SEQ ID NO: 9) | 72° C. |

The PCR amplification was performed using the Phusion High-Fidelity Taq Polymerase (Thermo Fisher, Waltham MA, USA) as described by the manufacturer. Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles.

The resulting fragment was cloned in pT7-7 ampicillin-resistant vector (Tabor and Richardson, 1985) using NdeI (CATATG) and HindIII (AAGCTT) as restriction cloning sites. *E. coli* strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 μg/ml).

The nifL gene was disrupted by the insertion of a kanamycin resistance cassette (Kan$^R$). The KIXX cassette, containing the Kan$^R$ gene and its own promoter (aph), excised with SmaI from pUC4-KIXX vector (Brewin et al., 1999), was inserted into the plasmid bearing the 2798 bp fragment, cut at restriction sites SalI and SmaI and filled in with Klenow DNA polymerase where necessary.

The KIXX cassette was inserted in both orientations: in same orientation and opposite orientation as nifLA transcription. The final constructs (Δ376::$p_{aph}$_KIXX and 4368::$p_{aph}$_KIXX) were transformed into *A. vinelandii* strain DJ, as described previously (Page and von Tigerstrom, 1978). $Kan^R$ transformants (5 μg/ml kanamycin) were screened for resistance to ampicillin ($Amp^R$; 100 μg/ml ampicillin); ampicillin-susceptible ($Amp^S$) derivatives were assumed to have arisen from a double-crossover recombination event, such that the wild-type nifL gene was replaced by the KIXX-containing DNA.

The Av368::$p_{aph}$_KIXX nifL with the KIXX cassette in the same orientation of nifLA transcription was impossible to construct, suggesting the apparent lethality of this mutant. The chromosomal insertion of the KIXX cassette in the opposite orientation of nifLA transcription (Av376::$p_{aph}$_KIXX strain) was successful and the deletion of the C-terminal quarter of the native NifL sequence were confirmed by PCR using and by sequencing.

Construction of the Av376::$p_{aph}$ strain—The Av376::$p_{aph}$ nifL mutant strain was obtained by gene disruption with the aph promoter sequence. DNA fragment containing the 1276 bp upstream and 1306 bp downstream genomic regions of the nifL bearing the SalI and SmaI restriction sites were obtained by PCR, using genomic DNA from *A. vinelandii* strain DJ. The primers nifL376-upstream-F-NdeI and nifL376-downstream-R-HindIII (see Table 2) were used for the amplification of a 2798 bp fragment.

The PCR amplification was performed using the Phusion High-Fidelity Taq Polymerase (Thermo Fisher, Waltham MA, USA) as described by the manufacturer. The resulting fragment was cloned in pT7-7 ampicillin-resistant vector (Tabor and Richardson 1985) using NdeI (CATATG) and HindIII (AAGCTT) as restriction cloning sites. *E. coli* strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 μg/ml).

The nifL gene was disrupted by the insertion of the aph promoter region of the KIXX cassette. The aph promoter region was isolated by PCR amplification using pUC4-KIXX vector (Brewin et al., 1999). The primers paph-F-SuraI and paph-R-SalI were used for the amplification of a 403 bp fragment. The aph promoter region (Δ03 bp fragment) was inserted into the plasmid bearing the 2798 bp fragment, cut at restriction sites SalI and SmaI, resulting into a molecular construct allowing the deletion of the C-terminal quarter of the native NifL sequence by the insertion of the aph promoter region in opposite orientation of nifLA transcription. The final construct (Δ376::$p_{aph}$) was used in congression crosses with Av376::$p_{aph}$_KIXX nifL mutant strain.

The transformation procedures employed were those described by Page and von Tigerstrom (1979). The selection marker used in the congression cross was a 1.7-kbp EcoRI fragment from pDB303 containing an rpoB mutation conferring rifampin resistance ($Rif^R$) (Premakumar et al., 1994). In order to favor transformation of mutagenized nifL::$p_{aph}$ DNA a ratio of at least 50 to 100 to 1 of mutant Δ376::$p_{aph}$ DNA construct to the DNA fragment having the rpoB mutation was used. $Rif^R$ transformants were selected on Burk medium containing rifampin (10 μg/ml) and subsequently screened for the loss of kanamycin resistance ($Kan^R$). Loss of kanamycin resistance indicated that the deletion of nifL with $p_{aph}$_KIXX was replaced by the DNA containing the nifL::$p_{aph}$ mutation through a double crossover event.

Construction of the Av376::$p_{cydA}$ and Av376::$p_{cycB}$ strains—The Av376::$p_{cydA}$ and Av376::$p_{cycB}$ mutant strains were obtained by gene disruption with cydA and cycB promoter sequences. DNA fragment containing the 1276 bp upstream and 1306 bp downstream genomic regions of the nifL bearing the SalI (GTCGAC) and SmaI (CCCGGG) restriction sites were obtained by PCR, using genomic DNA from *A. vinelandii* strain DJ. The primers nifL376-upstream-F-NdeI and nifL376-downstream-R-HindIII were used for the amplification of a 2798 bp fragment. The PCR amplification was performed using the Phusion High-Fidelity Taq Polymerase (Thermo Fisher, Waltham MA, USA) as described by the manufacturer.

The resulting fragment was cloned in pT7-7 ampicillin-resistant vector (Tabor and Richardson 1985) using NdeI (CATATG) and HindIII (AAGCTT) as restriction cloning sites. *E. coli* strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 μg/ml).

The nifL gene was disrupted by the insertion of the cydA ($p_{cydA}$) (Moshiri et al., 1991) and cycB ($p_{cycB}$) (Rey and Maier, 1997) promoter regions. The cydA and cycB promoter regions were isolated by PCR amplification using genomic DNA from *A. vinelandii* strain DJ. The primers $p_{cydA}$-F-SmaI and $p_{cydA}$-R-SalI, $p_{cycB}$-F-SmaI and $p_{cycB}$-R-SalI, were used for the amplification of 602 bp and 160 bp fragments respectively. The cydA and cycB promoter regions were inserted into the plasmid bearing the 2798 bp fragment, cut at restriction sites SmaI (CCCGGG) and SalI (GTCGAC), resulting into a molecular constructs allowing the deletion of the C-terminal quarter of the native NifL sequence by the insertion of the cydA and cycB promoter regions in opposite orientation of nifLA transcription.

The final constructs (Δ376::$p_{cydA}$ and 4376::$p_{cycB}$) were used in congression crosses with Av376::$p_{aph}$_KIXX nifL mutant strain. The transformation procedures employed were those described by Page and von Tigerstrom (1979). The selection marker used in the congression cross was a 1.7-kbp EcoRI fragment from pDB303 containing an rpoB mutation conferring rifampin resistance ($Rif^R$) (Premakumar et al., 1994). In order to favor transformation of mutagenized nifL::$p_{cydA}$ and nifL::$p_{cycB}$ DNA a ratio of at least 50 to 100 to 1 of 4376::$p_{cydA}$ or 4376::$p_{cycB}$ DNA construct to the DNA fragment having the rpoB mutation was used. $Rif^R$ transformants were selected on Burk medium containing rifampin (10 μg/ml) and subsequently screened for the loss of kanamycin resistance ($Kan^R$). Loss of kanamycin resistance indicated that the deletion of nifL with $p_{aph}$_KIXX was replaced by the DNA containing the nifL:$p_{cydA}$ or nifL:$p_{cycB}$ mutation through a double crossover event Construction of the Av376::KIXX strain—The Av376::KIXX nifL mutant strain was obtained by gene disruption with an insertion of an antibiotic resistance cassette KIXX between the SalI and SmaI sites, thereby removing the C-terminal quarter of the native NifL sequence. DNA fragment containing the 1276 bp upstream and 1306 bp downstream genomic regions of the nifL (see supplemental material) bearing the SalI (GTCGAC) and SmaI (CCCGGG) restriction sites were obtained by PCR, using genomic DNA from *A. vinelandii* strain DJ. Specific primers nifL376- upstream-F-NdeI and nifL376-downstream-R-HindIII (see Table 2) were used for the amplification of a 2798 bp fragment.

The PCR amplification was performed using the Phusion High-Fidelity Taq Polymerase (Thermo Fisher, Waltham MA, USA) as described by the manufacturer. Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles.

The resulting fragment was cloned in pT7-7 ampicillin-resistant vector (Tabor and Richardson, 1985) using NdeI (CATATG) and HindIII (AAGCTT) as restriction cloning sites. E. coli strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml).

The nifL gene was disrupted by the insertion of a kanamycin resistance cassette ($Kan^R$). The KIXX cassette, containing the $Kan^R$ gene, was PCR amplified from from pUC4-KIXX vector (Brewin et al., 1999), with the following specific primers KIXX-F-SmaI and KIXX-R-SalI using the Phusion High-Fidelity Taq Polymerase (Thermo Fisher, Waltham MA, USA) as described by the manufacturer. The KIXX cassette was inserted into the plasmid bearing the 2798 bp fragment, cut at restriction sites SalI and SmaI. The KIXX cassette was inserted in the opposite orientation as nifLA transcription.

The final construct (Δ376::KIXX) was transformed into A. vinelandii strain DJ, as described previously (Page and von Tigerstrom, 1978). $Kan^R$ transformants (5 µg/ml kanamycin) were screened for resistance to ampicillin ($Amp^R$; 100 µg/ml ampicillin); ampicillin-susceptible ($Amp^S$) derivatives were assumed to have arisen from a double-crossover recombination event, such that the wild-type nifL gene was replaced by the KIXX-containing DNA.

The Av376::KIXX nifL with the KIXX cassette in the same orientation of nifLA transcription was impossible to construct, suggesting the apparent lethality of this mutant. The chromosomal insertion of the KIXX cassette in the opposite orientation of nifLA transcription (Av376::KIXX strain) was successful and the deletion of the C-terminal quarter of the native NifL sequence were confirmed by PCR using and by sequencing.

Construction of the Δ376 strain—DNA fragment containing the 1276 bp upstream and 1306 bp downstream genomic region of the nifL region bearing the SalI (GTCGAC) and SmaI (CCCGGG) restriction sites were obtained by PCR, using genomic DNA from A. vinelandii strain DJ. Specific primers nifL376-upstream-F-NdeI and nifL376-downstream-R-HindIII (see Table 2) were used for the amplification of a 2798 bp fragment. The PCR amplifications were performed using the Phusion High-Fidelity Taq Polymerase (Thermo Fisher, Waltham MA, USA) as described by the manufacturer.

Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles.

The resulting fragment was cloned in pT7-7 ampicillin-resistant vector (Tabor and Richardson, 1985) using NdeI (CATATG) and HindIII (AAGCTT) as restriction cloning sites. E. coli strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml).

The final construct (Δ376) was used in congression crosses with Av376::$p_{aph}$KIXX nifL mutant strain. The transformation procedures employed were those described by Page and von Tigerstrom (1979). The selection marker used in the congression cross was a 1.7-kbp EcoRI fragment from pDB303 containing an rpoB mutation conferring rifampin resistance ($Rif^R$) (Premakumar et al., 1994). In order to favor transformation of mutagenized 4376 DNA a ratio of at least 50 to 100 to 1 of 4376 DNA construct to the DNA fragment having the rpoB mutation was used.

$Rif^R$ transformants were selected on Burk medium containing rifampin (10 µg/ml) and subsequently screened for the loss of kanamycin resistance ($Kan^R$). Loss of kanamycin resistance indicated that the deletion of nifL with $p_{aph}$_KIXX was replaced by the DNA containing the 4376 mutation through a double crossover event.

B. Deletion of the PAS1/PAS2 Domains of NifL: Av371::$p_{aph}$KIXX/Av372::$p_{aph}$KIXX/Δ371 Strains Construction of the Av371::$p_{aph}$_KIXX and the Av372::$p_{aph}$_KIXX strains—The Av371::$p_{aph}$_KIXX and Av372::$p_{aph}$_KIXX nifL mutant strains were obtained by gene disruption with an insertion of an antibiotic resistance cassette KIXX between the two BglII sites, thereby removing the N-terminal domain (PAS1 and PAS2 domains) of the native NifL sequence. DNA fragment containing the 1534 bp upstream and 1565 bp downstream genomic regions of the nifL from the two BglII (AGATCT) restriction sites were obtained by PCR, using genomic DNA from A. vinelandii strain DJ. Specific primers nifL371-upstream-F-NdeI/nifL371-upstream-R-EcoRI and nifL371-downstream-F-EcoRI/nifL371-downstream-R-HindIII (see Table 2) were used for the amplification of the 1534 bp upstream and 1565 bp downstream fragments respectively.

The PCR amplifications were performed using the Phusion High-Fidelity Taq Polymerase (Thermo Fisher, Waltham MA, USA) as described by the manufacturer. Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles.

The resulting fragments were cloned in pT7-7 ampicillin-resistant vector respectively (Tabor and Richardson, 1985) using NdeI (CATATG)/EcoRI (GAATTC) and EcoRI (GAATTC)/HindIII (AAGCTT) as restriction cloning sites. E. coli strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml and kanamycin used 50 µg/ml).

The nifL gene was disrupted by the insertion of a kanamycin resistance cassette ($Kan^R$). The KIXX cassette, containing the $Kan^R$ gene and its own promoter (aph), was PCR amplified from pUC4-KIXX vector (Brewin et al., 1999), with the following specific primers $p_{aph}$_KIXX-F-EcoRI and $p_{aph}$_KIXX-R-EcoRI using the Phusion High-Fidelity Taq Polymerase (Thermo Fisher, Waltham MA, USA) as described by the manufacturer. The KIXX cassette was inserted into the plasmid bearing the 1534 bp upstream and 1565 bp downstream genomic regions of the nifL cut at restriction site EcoRI. The KIXX cassette was inserted in both orientations: in same orientation and opposite orientation as nifLA transcription.

The final constructs were transformed into *A. vinelandii* strain DJ, as described previously (Page and von Tigerstrom, 1978). Kan$^R$ transformants (5 µg/ml kanamycin) were screened for resistance to ampicillin (Amp$^R$; 100 µg/ml ampicillin); ampicillin-susceptible (Amp$^S$) derivatives were assumed to have arisen from a double-crossover recombination event, such that the wild-type nifL gene was replaced by the KIXX-containing DNA.

The Av372::p$_{aph}$_KIXX nifL with the KIXX cassette in the same orientation of nifLA transcription was impossible to construct, suggesting the apparent lethality of this mutant. The chromosomal insertion of the KIXX cassette in the opposite orientation of nifLA transcription was successful and the deletion of the C-terminal quarter of the native NifL sequence were confirmed by PCR using and by sequencing.

Construction of the Δ371 strain—DNA fragments containing the 1534 bp upstream and 1565 bp downstream genomic regions of the nifL from the two BglII (AGATCT) restriction sites were obtained by PCR, using genomic DNA from *A. vinelandii* strain DJ. Specific primers nifL371-upstream-F-NdeI/nifL371-upstream-R-EcoRI and nifL371-downstream-F-EcoRI/nifL371-downstream-R-HindIII (see Table 2) were used for the amplification of the 1534 bp upstream and 1565 bp downstream fragments respectively. The PCR amplifications were performed using the Phusion High-Fidelity Taq Polymerase (Thermo Fisher, Waltham MA, USA) as described by the manufacturer.

Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles. The resulting fragments were cloned in pT7-7 ampicillin-resistant vector respectively (Tabor and Richardson, 1985), using NdeI (CATATG)/EcoRI (GAATTC) and EcoRI (GAATTC)/HindIII (AAGCTT) as restriction cloning sites (Δ371 construct).

*E. coli* strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml). The final construct (Δ371) was used in congression crosses with Av371::p$_{aph}$_KIXX nifL mutant strain. The transformation procedures employed were those described by Page and von Tigerstrom (1979). The selection marker used in the congression cross was a 1.7-kbp EcoRI fragment from pDB303 containing an rpoB mutation conferring rifampin resistance (Rif$^R$) (Premakumar et al., 1994). In order to favor transformation of mutagenized Δ371 DNA a ratio of at least 50 to 100 to 1 of Δ371 DNA construct to the DNA fragment having the rpoB mutation was used.

Rif$^R$ transformants were selected on Burk medium containing rifampin (10 µg/ml) and subsequently screened for the loss of kanamycin resistance (Kan$^R$). Loss of kanamycin resistance indicated that the deletion of nifL with p$_{aph}$_KIXX was replaced by the DNA containing the Δ371 mutation through a double crossover event.

C. Deletion of the Central Domains of NifL: Av346::p$_{aph}$_HIXX/Av345::p$_{aph}$_KIXX/Δ346 Strains Construction of the Av346::p$_{aph}$_KIXX and the Av345::p$_{aph}$_KIXX strains—The Av346::p$_{aph}$_KIXX and Av345::p$_{aph}$_KIXX nifL mutant strains were obtained by gene disruption with an insertion of an antibiotic resistance cassette KIXX between the NotI (GCGGCCGC) and BcnI (TGATCA) sites, thereby removing the central domain of the native NifL sequence. DNA fragments containing the 1536 bp upstream and 1565 bp downstream genomic regions of the nifL from the NotI (GCGGCCGC) and BcnI (TGATCA) restriction sites were obtained by PCR, using genomic DNA from *A. vinelandii* strain DJ. Specific primers nifL346-upstream-F-NdeI/nifL346-upstream-R-EcoRI and nifL346-downstream-F-EcoRI/nifL346-downstream-R-HindIII (see Table 2) were used for the amplification of the 1536 bp upstream and 1565 bp downstream fragments respectively. The PCR amplifications were performed using the Phusion High-Fidelity Taq Polymerase (Thermo Fisher, Waltham MA, USA) as described by the manufacturer.

Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles. The resulting fragments were cloned in pT7-7 ampicillin-resistant vector respectively (Tabor and Richardson, 1985) using NdeI (CATATG)/EcoRI (GAATTC) and EcoRI (GAATTC)/HindIII (AAGCTT) as restriction cloning sites.

*E. coli* strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml). The nifL gene was disrupted by the insertion of a kanamycin resistance cassette (Kan$^R$). The KIXX cassette, containing the Kan$^R$ gene and its own promoter (aph), was PCR amplified from pUC4-KIXX vector (Brewin et al., 1999), with the following specific primers p$_{aph}$_KIXX-F-EcoRI and p$_{aph}$_KIXX-R-EcoRI using the Phusion High-Fidelity Taq Polymerase (Thermo Fisher, Waltham MA, USA) as described by the manufacturer.

The KIXX cassette was inserted into the plasmid bearing the 1534 bp upstream and 1565 bp downstream genomic regions of the nifL cut at restriction site EcoRI. The KIXX cassette was inserted in both orientations: in same orientation and opposite orientation as nifLA transcription.

The final constructs were transformed into *A. vinelandii* strain DJ, as described previously (Page and von Tigerstrom, 1978). Kan$^R$ transformants (5 µg/ml kanamycin) were screened for resistance to ampicillin (Amp$^R$; 100 µg/ml ampicillin); ampicillin-susceptible (Amp$^S$) derivatives were assumed to have arisen from a double-crossover recombination event, such that the wild-type nifL gene was replaced by the KIXX-containing DNA.

The Av345::p$_{aph}$_KIXX nifL with the KIXX cassette in the same orientation of nifLA transcription was impossible to construct, suggesting the apparent lethality of this mutant. The chromosomal insertion of the KIXX cassette in the opposite orientation of nifLA transcription (Av346::p$_{aph}$_KIXX strain) was successful and the deletion of the C-terminal quarter of the native NifL sequence were confirmed by PCR using and by sequencing.

Construction of the Av346 strain—DNA fragments containing the 1536 bp upstream and 1565 bp downstream genomic regions of the nifL from the NotI (GCGGCCGC) and BcnI (TGATCA) restriction sites were obtained by PCR, using genomic DNA from *A. vinelandii* strain DJ. Specific primers nifL346-upstream-F-NdeI/nifL346-upstream-R-EcoRI and nifL346-downstream-F-EcoRI/nifL346-downstream-R-HindIII (see Table 2) were used for the amplification of the 1536 bp upstream and 1565 bp downstream fragments respectively. The PCR amplifications were performed using the Phusion High-Fidelity Taq Polymerase (Thermo Fisher, Waltham MA, USA) as described by the manufacturer.

Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles.

The resulting fragments were cloned in pT7-7 ampicillin-resistant vector respectively (Tabor and Richardson, 1985), using NdeI (CATATG)/EcoRI (GAATTC) and EcoRI (GAATTC)/HindIII (AAGCTT) as restriction cloning sites (Δ346 construct).

E. coli strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml). The final construct (Δ346) was used in congression crosses with Av346::$p_{aph}$_KIXX nifL mutant strain. The transformation procedures employed were those described by Page and von Tigerstrom (1979). The selection marker used in the congression cross was a 1.7-kbp EcoRI fragment from pDB303 containing an rpoB mutation conferring rifampin resistance ($Rif^R$) (Premakumar et al., 1994).

In order to favor transformation of mutagenized 4346 DNA a ratio of at least 50 to 100 to 1 of 4346 DNA construct to the DNA fragment having the rpoB mutation was used. $Rif^R$ transformants were selected on Burk medium containing rifampin (10 µg/ml) and subsequently screened for the loss of kanamycin resistance ($Kan^R$). Loss of kanamycin resistance indicated that the deletion of nifL with $p_{aph}$_KIXX was replaced by the DNA containing the 4346 mutation through a double crossover event.

D. Deletion of the Whole NifL: ΔnifL::$p_{aph}$_KIXX Strain

Construction of the ΔnifL::$p_{aph}$_KIXX strain. The ΔnifL: $p_{aph}$_KIXX nifL mutant strain was obtained by gene disruption with an insertion of an antibiotic resistance cassette KIXX removing the whole nifL gene. DNA fragments containing the 1000 bp upstream genomic region from the ATG of nifL gene and the 1000 bp downstream genomic region of TGA of the nifL gene were obtained by PCR, using genomic DNA from A. vinelandii strain DJ. Specific primers nifL-upstream-F-NdeI/nifL346-upstream-R-BamHI and nifL-downstream-F-BamHI/nifL-downstream-R-HindIII (see Table 2) were used for the amplification of the 1000 bp upstream and 1000 bp downstream fragments respectively. The PCR amplifications were performed using the Phusion High-Fidelity Taq Polymerase (Thermo Fisher, Waltham MA, USA) as described by the manufacturer.

Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (c) 72° C. for 2 min (elongation). A final single step at 72° C. for 10 min followed these 35 cycles. The resulting fragments were cloned in pT7-7 ampicillin-resistant vector respectively (Tabor and Richardson, 1985) using NdeI (CATATG)/BamHI (GGATCC) and BamHI (GGATCC)/HindIII (AAGCTT) as restriction cloning sites (construct ΔnifL::$p_{aph}$_KIXX).

E. coli strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml). The nifL gene was disrupted by the insertion of a kanamycin resistance cassette ($Kan^R$).

The KIXX cassette, containing the $Kan^R$ gene and its own promoter (aph), excised with BamHI from pUC4-KIXX vector (Brewin et al., 1999), was inserted into the plasmid bearing the 1000 bp upstream genomic region from the ATG of nifL gene and the 1000 bp downstream genomic region of TGA of the nifL gene, cut at restriction site BamHI. The KIXX cassette was inserted in both orientations: in same orientation and opposite orientation as nifLA transcription. The final construct (ΔnifL;:$p_{aph}$_KIXX) was transformed into A. vinelandii strain DJ, as described previously (Page and von Tigerstrom, 1978).

$Kan^R$ transformants (5 µg/ml kanamycin) were screened for resistance to ampicillin ($Amp^R$; 100 µg/ml ampicillin); ampicillin-susceptible ($Amp^S$) derivatives were assumed to have arisen from a double-crossover recombination event, such that the wild-type nifL gene was replaced by the KIXX-containing DNA. The chromosomal insertion of the KIXX cassette in the opposite orientation of nifLA transcription (ΔnifL:$p_{aph}$_KIXX strain) was successful and the deletion of the whole native NifL sequence were confirmed by PCR using and by sequencing.

E. Deletion of the N-Terminal, Central, and C-Terminal Domains of the Native NifL Sequence: AvFM371-376:: $p_{aph}$_KIXX nifL Strain Construction of the AvFM371-376::$p_{aph}$_KIXX The AvFM371-376::$p_{aph}$_KIXX nifL mutant strain was obtained by gene disruption with an insertion of an antibiotic resistance cassette KIXX between the BglII and SmaI sites, thereby removing the N-terminal, central, and C-terminal domains of the native NifL sequence. DNA fragment containing the 1534 bp upstream and 1306 bp downstream genomic regions of the nifL bearing the BglII (AGATCT) and SmaI (CCCGGG) restriction sites were obtained by PCR, using genomic DNA from A. vinelandii strain DJ. Specific primers nifL371-upstream-F-NdeUnifL371-upstream-R-EcoRI and nifL376-downstream-F-EcoRI/nifL376-downstream-R-HindIII (see Table 2) were used for the amplification of the 1534 bp upstream and 1306 bp downstream fragments respectively.

The PCR amplifications were performed using the Phusion High-Fidelity Taq Polymerase (Thermo Fisher, Waltham MA, USA) as described by the manufacturer. Amplification was performed using the following cycling parameters: an initial single step at 98° C. for 30 s (denaturation) was followed by 35 cycles of the following: (a) 98° C. for 10 sec (denaturation), (b) 64° C. for 30 sec, and (C) 72° C. for 2 min (elongation). A final single step at 72° C. for 10 min followed these 35 cycles.

The resulting fragments were cloned in pT7-7 ampicillin-resistant vector respectively (Tabor and Richardson, 1985) using NdeI (CATATG)/EcoRI (GAATTC) and EcoRI (GAATTC)/HindIII (AAGCTT) as restriction cloning sites. E. coli strain JM109 (Promega, Madison, WI, USA) was used for cloning and was grown in Luria-Bertani medium (LB) (Bertani, 1951) at 37° C. and 250 rpm, supplemented with appropriate antibiotic (ampicillin used at 100 µg/ml and kanamycin used 50 µg/ml).

The nifL gene was disrupted by the insertion of a kanamycin resistance cassette ($Kan^R$). The KIXX cassette, containing the $Kan^R$ gene and its own promoter (aph), was PCR amplified from pUC4-KIXX vector (Brewin et al., 1999), with the following specific primers $p_{aph}$_KIXX-F-EcoRI and $p_{aph}$_KIXX-R-EcoRI using the Phusion High-Fidelity Taq Polymerase (Thermo Fisher, Waltham MA, USA) as described by the manufacturer. The KIXX cassette was inserted into the plasmid bearing the 1534 bp upstream and 1306 bp downstream genomic regions of the nifL cut at restriction site EcoRI. The KIXX cassette was inserted in both orientations: in same orientation and opposite orientation as nifLA transcription.

The final constructs were transformed into *A. vinelandii* strain DJ, as described previously (Page and von Tigerstrom, 1978). $Kan^R$ transformants (5 µg/ml kanamycin) were screened for resistance to ampicillin ($Amp^R$; 100 µg/ml ampicillin); ampicillin-susceptible ($Amp^S$) derivatives were assumed to have arisen from a double-crossover recombination event, such that the wild-type nifL gene was replaced by the KIXX-containing DNA.

The chromosomal insertion of the KIXX cassette in the opposite orientation of nifLA transcription was successful and the combine deletion of the N-terminal, central, and C-terminal domains of the native NifL sequence were confirmed by PCR and by sequencing.

2. Measuring Ammonia Excretion by nifL Mutants

*A. vinelandii* strain DJ (wild-type strain; obtained from Dennis Dean, Virginia Tech, VA, USA) (Setubal et al., 2009) and nifL mutants (this example) were grown on aerobically at 30° C. in Burk's sucrose medium (B medium) (Toukdarian and Kennedy, 1986). B medium is an ammonium-free medium; growth in this medium is referred to here as diazotrophic conditions.

Two-hundred-milliliter liquid cultures, contained in 500-ml Erlenmeyer flasks, were incubated on a rotary shaker at 180 rpm. Samples of cultures were taken at different times, centrifuged (14,000×g for 5 min) and filtered (through cellulose acetate membranes; pore size, 0.25 um). Appropriate amounts of filtrated supernatant were tested for the presence of ammonium by the indophenol method (Bergersen, 1980). This consisted of the addition, in order, of 0.5 ml of phenol-sodium nitroprusside solution (phenol, 50 g $liter^{-1}$; sodium nitroprusside, 0.25 g 0.5 ml of sodium hypochlorite solution (0.1 M), and 0.1 ml of sample.

The mixture was incubated for 30 min at room temperature. The A625 was measured, and the ammonium concentration was estimated from a standard curve obtained with ammonium solutions at various concentrations assayed with the same reagent solutions. Harvested cell pellets were disrupted by one cycle of sonication (7 W, 50 s; ultrasonic homogenizer, model 3000; Biologics, Inc., Cary, NC, USA). Protein assays were performed on the same cell lysate for each time point and tested condition.

Protein was quantified using the Coomassie protein assay from Thermo Scientific (Waltham, MA, USA). Thirty microliters of sample was mixed with 1.5 ml of Thermo Scientific reagent and incubated at room temperature for 10 min. The absorbance at 595 nm was measured using a spectrophotometer (Thermo Spectronic BioMate 3; Thermo Scientific). The protein content of the sample was calculated using a standard curve (albumin standard used as described by the manufacturer).

Culture supernatants of wild-type strain and nifL mutants grown aerobically at 30° C. on Burk's sucrose medium were tested for the presence of ammonium. Av376::$p_{aph}$ KIXX, Av376::$p_{aph}$, Av376::$p_{cydA}$ and Av376::$p_{cycB}$ excreted ammonium rather toward the end of exponential growth. The mean level of ammonium excreted nifL mutants strains stationary phase cultures was up to 10 mM.

Example 2

Transfer of Ammonia from Engineered Mutant Strains to Crop Plants

In this example, we demonstrate, using $^{15}N_2$ gas enrichment experiments, that the *Azotobacter vinelandii* nifL mutants disclosed in Example 1 can facilitate the uptake by non-leguminous plants (in this case, rice) of substantial amounts of nitrogen originating in the atmosphere. The atmospheric nitrogen is fixed into the soil as excreted ammonia, as described in Example 1 above.

Accordingly, this example provides "proof of principle" that the disclosed ammonia excreting mutants can be used in inoculants/biofertilizers that can be applied to soil, plants or seeds to enhance the growth of the plants, by providing a source of bioavailable nitrogen. This would substantially decrease the need for applying chemical nitrogen fertilizers to provide bioavailable nitrogen. This is a significant advance for the sustainable production of non-leguminous crop plants that are not capable of forming symbiotic relationships with diazotrophic bacteria.

$^{15}N$ external labeling or enrichment (usually expressed as atom %) and $^{15}N$ naturally occurring abundance ($\delta^{15}N$, ‰) techniques have been employed to trace the direction and magnitude of N transfer between diazotrophic bacteria and plants. The transfer of $^{15}N_2$ from bacteria to the plant tissues demonstrates the potential of this diazotrophic community to contribute to the nitrogen nutrition of the plant, fulfill, at least in part, the reduced nitrogen requirements of the plant.

Figure 6:
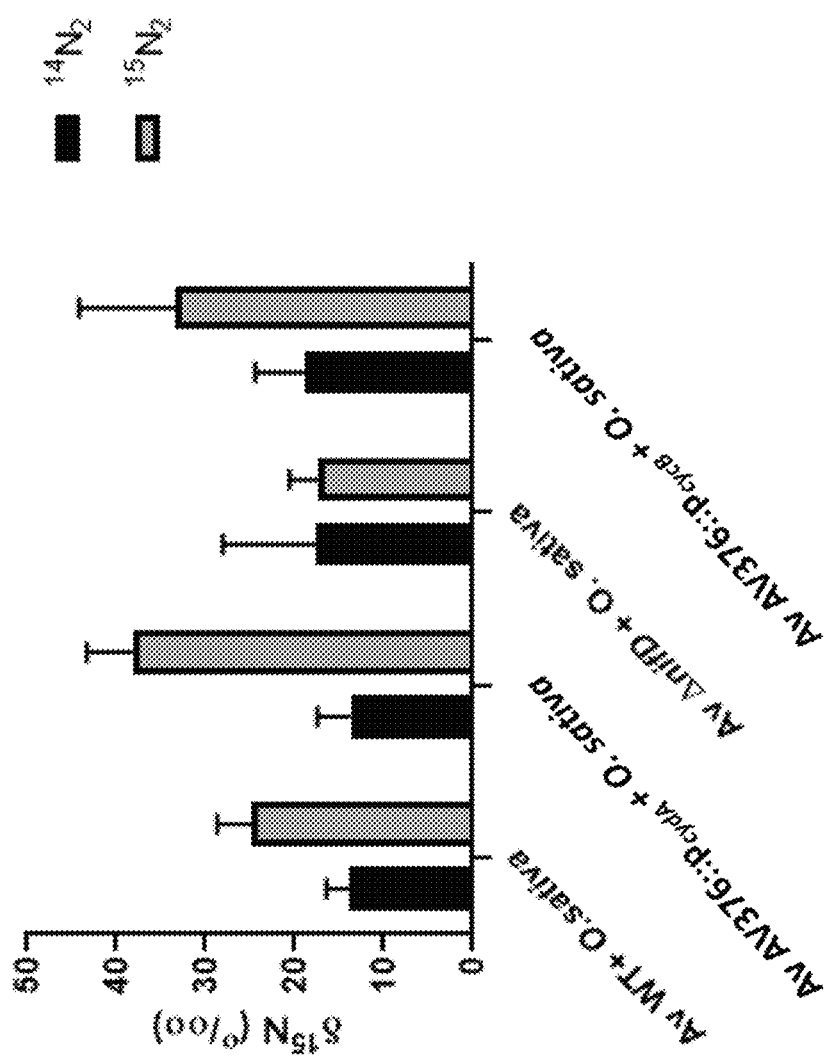
FIG. 6. $^{15}N$ incorporation experiments on rice plants (Oryza sativa) inoculated with A. vinelandii WT strain (Av WT), A. vinelandii AV376::$p_{cydA}$ strain, A. vinelandii nifD mutant (Av ΔnifD), and A. vinelandii AV376::$p_{cycB}$ strain.

Significant differences were observed in $^{15}N$-incorporation into rice plants between rice plants inoculated with *A. vinelandii* wild type strain and rice plants inoculated with ammonium excreting nifL strains. Quantification of $^{15}N$ incorporated into plant tissues demonstrated that the ammonium excreting nifL (AV346::$p_{aph}$–KIXX; AV376::$p_{aph}$–KIXX; AV346::$p_{aph}$; AV376::$p_{cydA}$ and AV376::$p_{cycB}$) strains stimulate significantly the transfer of fixed nitrogen to the plants, confirming the effect of a plant growth promoting factor provided by these nifL mutant engineered strains (FIG. 6).

Figure 7:
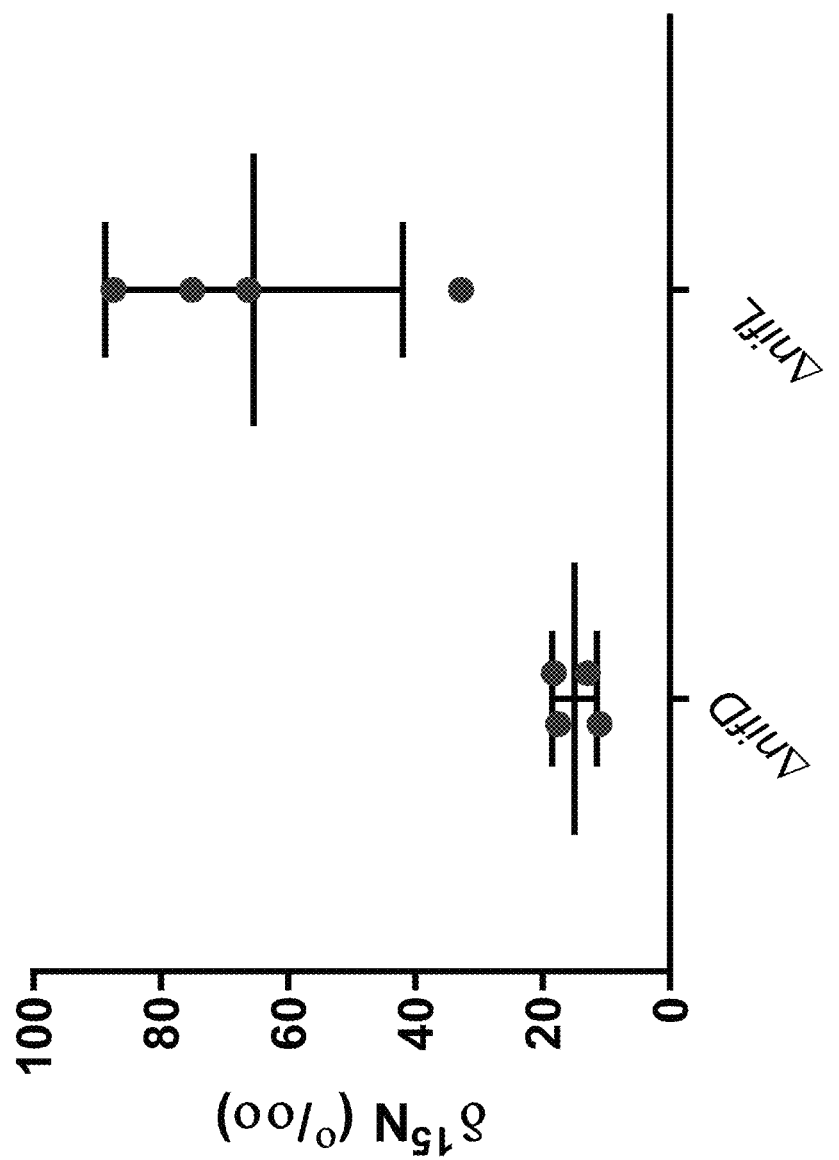
FIG. 7. $^{15}N_2$ enrichment experiment of rice (Oryza sativa) seedlings incubated with Azotobacter vinelandii strains. 4 technical replicates, p-value<0.01.

This conclusion also consistent with additional data obtained from four replicates of $^{15}N_2$ enrichment experiments also performed in rice (*Oryza sativa*) (see FIG. 7).

Notably, engineered *A. vinelandii* strains, AV376::$p_{cydA}$ and AV376::$p_{cycB}$, have been developed to not have any antibiotic resistance marker and to not have any foreign gene, constituting ideal biofertilizers strains suitable for agricultural practices.

In sum, this example demonstrates that the unique property of the disclosed ammonium excreting strains can be successfully used to enhance and sustain biological nitrogen fixation in agricultural systems.

Materials and Methods

Sterilization and Germination of Rice Seeds

Outer coat of about 100 rice seeds were removed and treated with 2% bleach solution for 15 min in a 50 ml falcon tube taped to a table top shaker. Subsequently, the bleach was poured out under the hood into a plastic waste container and then rinsed the seeds by 5 times by sterile milliQ water. About 20 ml of water was kept from the last wash and the tube was covered with the aluminum foil and taped it to the shaker for overnight at room temperature. Next day, the rice seeds are spread on a sterile wet germination paper in a plate using sterilized forceps. These plates were wrapped with parafilm and incubated at room temperature for three days to germinate.

Putting Rice Seeds in the Pouch

A plastic bucket and a stand to keep the germination pouch were sprayed with ethanol under the hood and let it stand under the hood for 15 minutes with UV light on. Thereafter, using the forceps to open the area between the pouches and the plastic, sterile milliQ water was added into the pouch. After doing this for all the pouches, the pouches were allowed to get wet entirely for 5 minutes.

Next, germinated rice seeds were put into the holes of the germination pouch by placing the seed facing root downward and the shoot facing upward, using the forceps to dig into the pouches in order to make sure the seed is oriented correctly. About 7 seeds were placed into each germination pouch set. After placing the seeds in the pouches, the pouches, the stand with the pouches was placed into the sterile plastic bucket. Then sterile milliQ water was added to the bucket to keep some moisture to avoid drying of the seedlings. The plastic bucket was put into the chamber for a week under 16 hours of light and 8 hours of dark at 22 C.

Co-Culture of Rice Seedlings and *A. vinelandii* Strains

After a week of rice seedling growing in the growth chambers, the plastic bucket were taken to the hoods. With the help of sterile forceps, the area between the plastic and the germination paper was opened and the 48 hour old cultures of respective *A. vinelandii* strains were added individually in to the pouches. This step was done carefully in order to not to touch the plants with the bacterial culture.

Thereafter, each pouch was put into Supelco Push-pull gas bag which was sealed with the help of heat sealer. After making sure that the valve in the bag was locked, either about 2% of $^{15}N_2$ or $^{14}N_2$ gas was added to the bags. Repeating these steps, all the pouches were prepared in the similar way and carefully labeled. Thereafter, the bags were put into the growth chamber for a week at 22° C. (16 h light and 8 h dark).

Sampling for Isotope Ratio Mass Spectrometry

After a week of co-culture, the bags were cut open and the shoots were harvested with sterile razor blades and put into an envelope. These envelopes were dried at 65° C. for three days. Thereafter, the dried shoots were powdered using metal balls and bead beater machine. These powdered samples were weighed into tin foils and submitted to mass spectrometry facility in soil science at UW-Madison.

Example 3

Transfer of Ammonia from Engineered Mutant Strains to Mycorrhizal Fungi

Mycorrhizal fungi have been shown to acquire nitrogen from the soil (in the form of ammonium/ammonia) and transfer it to plants. In this example, we demonstrate, using $^{15}N_2$ gas enrichment experiments, that the *Azotobacter vinelandii* nifL mutants disclosed in Example 1 can facilitate the uptake by mycorrhizal fungi of large amounts of atmospheric nitrogen that is fixed by the mutants as excreted ammonia, as described in Example 1 above.

Accordingly, this example provides "proof of principle" that co-cultures of the disclosed ammonia excreting mutants and mycorrhizal fungi can also be used in inoculants/biofertilizers that can be applied to soil, plants or seeds to enhance the growth of the plants, by providing a source of bioavailable nitrogen.

More specifically, this data suggests that the disclosed nifL-modified diazotrophic γ-proteobacteria can be combined with mycorrhizal fungi to transfer nitrogen to plants in 2 steps: the nifL-modified bacteria produce ammonia that is taken up by the mycorrhizal fungi, and the mycorrhizal fungi subsequently function to facilitate the delivery of the fixed nitrogen to plants.

As demonstrated in Example 1, the nifL-modified bacteria produce and leak large amounts of ammonium into the surrounding medium. However, most plants don't utilize ammonium well as a source of nitrogen. The "mixed inoculants" of mycorrhizal fungi and diazotrophic nifL-modified bacteria would facilitate effective use of the fixed nitrogen by plants, in that the diazotrophic nifL-modified bacteria could produce ammonia from nitrogen in the air, and the mycorrhizal fungi could take up the ammonia and deliver it to the plants in a bioavailable form.

We performed three sets of $^{15}N_2$ gas enrichment experiments similar to those reported in Example 2, except that we measured nitrogen uptake in two different mycorrhizal fungi species (*Laccaria* bicolor and *Hebeloma cylindrosporum*) that were co-cultured with *A. vinelandii* wild-type and nifL mutant bacteria.

Figure 8:
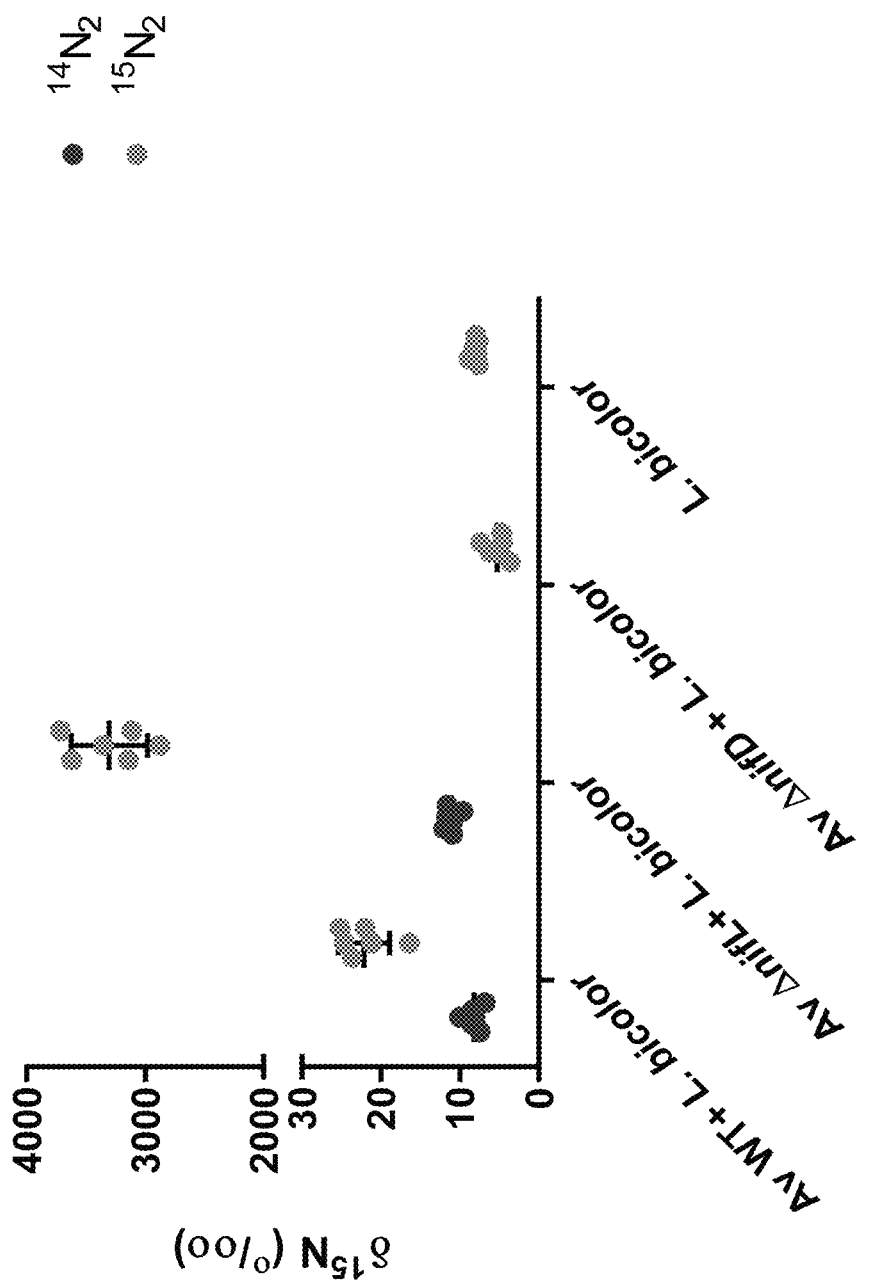
FIG. 8. Results of a $^{15}N$ enrichment experiments of the mycorrhizal fungus Laccaria bicolor co-cultured with mutant and wild type A. vinelandii strains.
Figure 9:
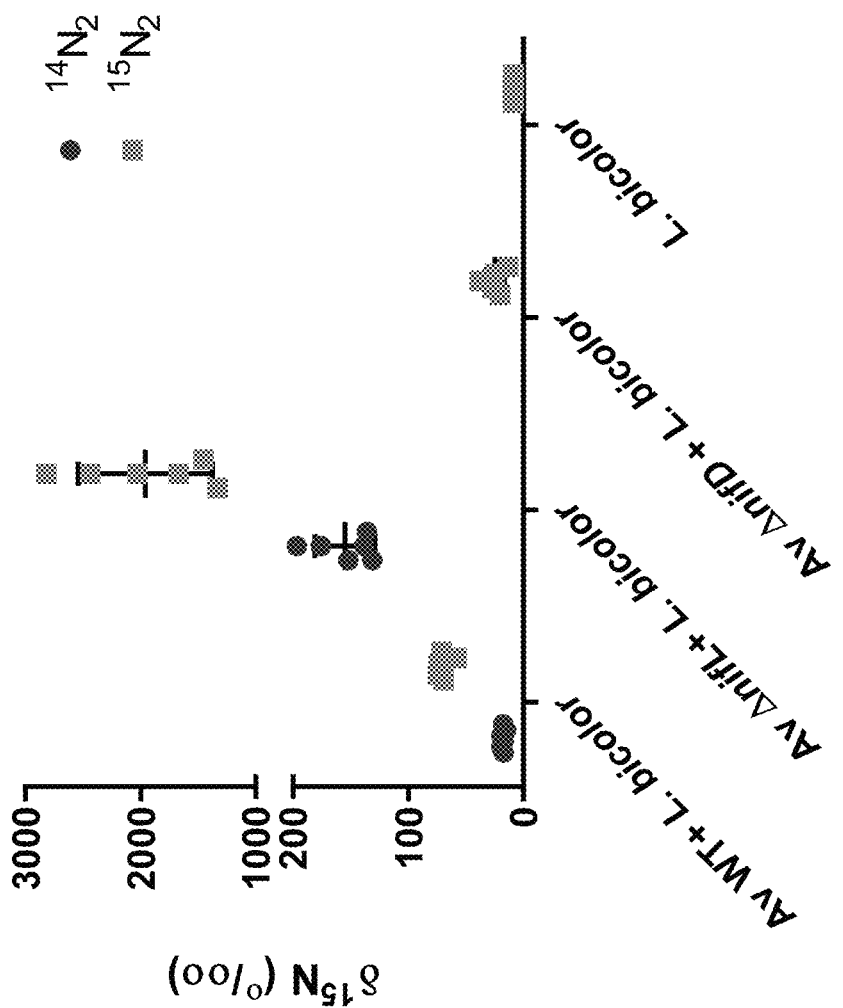
FIG. 9. Results of $^{15}N$ enrichment experiments of the mycorrhizal fungus Laccaria bicolor co-cultured with mutant and wild type A. vinelandii strains.
Figure 10:
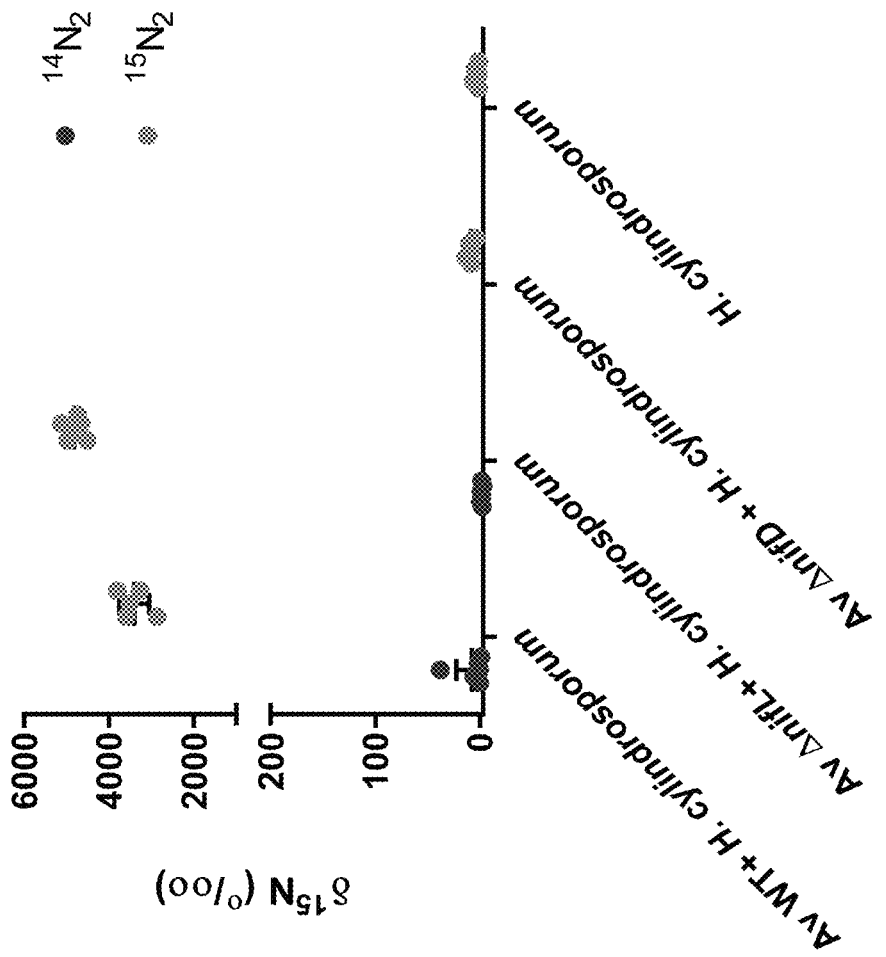
FIG. 10. Results of $^{15}N$ enrichment experiments of the mycorrhizal fungus Hebeloma cylindrosporum co-cultured with mutant and wild type A. vinelandii strains.

Quantification of $^{15}N$ incorporated into the mycorrhizal fungi demonstrated that large amounts of fixed nitrogen are transferred from the ammonium excreting nifL (AvΔnifL) to the mycorrhizal fungi, as compared to wild type (AvWT) and control (AvΔnifD) bacteria (see FIGS. 8, 9 and 10).

In sum, this data suggests that mycorrhizal fungi can be used in a co-culture with the disclosed genetically modified ammonia excreting bacteria to facilitate the transfer of the ammonia as a fixed nitrogen source to plants.

Example 4

Ammonia Excreting Strains are Supported by Multiple Different Carbon Sources

*A. vinelandii* can use a variety carbon sources as growth substrates which can be found in root exudates of plant crops. The ability of *A. vinelandii* to excrete ammonium ion using glucose, sucrose, and galactose as different carbon sources has been tested. Our data showed that glucose, sucrose and galactose can support ammonium ion release from the ammonia excreting ΔnifL strains. The ability of the different ammonia excreting ΔnifL strains to grow on different carbon sources and release ammonium ion can be used to force the dependence of these strains on root exudates, thereby promoting the colonization of roots and reducing the persistence of bacteria in the environment after the growing season.

Materials and Methods

Culture supernatants of wild-type strain (wild-type strain; obtained from Dennis Dean, Virginia Tech, VA, USA) (Setubal et al., 2009) and nifL (this study) mutants grown aerobically at 30° C. on Burk's ammonium-free medium supplemented with sucrose, glucose or galactose (10 mM) were tested for the presence of ammonium. Two-hundred-milliliter liquid cultures, contained in 500-ml Erlenmeyer flasks, were incubated on a rotary shaker at 180 rpm. Samples of cultures were taken at different times, centrifuged (14,000×g for 5 min) and filtered (through cellulose acetate membranes; pore size, 0.25,um).

Appropriate amounts of filtrated supernatant were tested for the presence of ammonium by the indophenol method (Bergersen, 1980). This consisted of the addition, in order, of 0.5 ml of phenol-sodium nitroprusside solution (phenol, 50 g liter$^{-1}$; sodium nitroprusside, 0.25 g 0.5 ml of sodium hypochlorite solution (0.1 M), and 0.1 ml of sample. The mixture was incubated for 30 min at room temperature. The A625 was measured, and the ammonium concentration was estimated from a standard curve obtained with ammonium solutions at various concentrations assayed with the same reagent solutions.

Harvested cell pellets were disrupted by one cycle of sonication (7 W, 50 s; ultrasonic homogenizer, model 3000; Biologics, Inc., Cary, NC, USA). Protein assays were performed on the same cell lysate for each time point and tested condition. Protein was quantified using the Coomassie protein assay from Thermo Scientific (Waltham, MA, USA). Thirty microliters of sample was mixed with 1.5 ml of Thermo Scientific reagent and incubated at room temperature for 10 min. The absorbance at 595 nm was measured using a spectrophotometer (Thermo Spectronic BioMate 3; Thermo Scientific). The protein content of the sample was calculated using a standard curve (albumin standard used as described by the manufacturer).

Example 5

Transfer of Ammonia from Engineered Mutant Strains to Pine Trees

In an extension of the experiments reported above in Examples 2 and 3, we studied whether mycorrhizal fungi can be used to assist the ammonia-excreting *Azotobacter vinelandii* in facilitating nitrogen uptake in pine trees.

Our results showed that in the case of pine trees, nitrogen is effectively delivered taken and taken up by pine trees in the presence of the ammonia-excreting modified bacteria described above, without mycorrhizal fungi acting as intermediates. This study provides further evidence of the ability of the engineered ammonia-excreting disclosed herein to effectively transfer nitrogen from the air to a broad spectrum of plants (i.e., crop plants/cereal grains, as shown in rice in Example 2, and gymnosperms, as demonstrated in this Example).

Example 6

Transfer of Ammonia from Engineered Mutant Strains to Corn (Maize)

In a further extension of the experiments reported above in Examples 2 and 3, we studied whether mycorrhizal fungi can be used to assist the ammonia-excreting *Azotobacter vinelandii* in facilitating nitrogen uptake in corn.

Our results showed that in the case of corn, mycorrhizal fungi can effectively act to increase the delivery and uptake of nitrogen fixed by the engineered ammonia-excreting bacteria disclosed herein into the corn plant. Accordingly, this example provides further "proof of principle" that co-cultures of the disclosed ammonia excreting mutants and mycorrhizal fungi can also be used in inoculants/biofertilizers that can be applied to soil, plants or seeds to enhance the growth of the plants, by providing a source of bioavailable nitrogen.

Example 7 rfn1 Operon Upregulation in Exemplary Ammonia-Excreting Engineered Bacteria

FIG. 11 shows the organization and orientation of relevant genes in *A. vinelandii* DJ strain, the strain used in making the disclosed ammonia-excreting mutants. Adjacent to and upstream from nifL/nifA gene cluster (gene identification number for *A. vinelandii* DJ strain: Avin_50990, Avin_51000) is another gene cluster that encodes rnf1 (rnfA1, B1, C1, D1, G1, E1 and H1; gene identification number for *A. vinelandii* DJ strain: Avin_50920 to Avin_50980).

The rnf1 operon encodes an electron transport complex that has been shown to be important in converting chemiosmotic potential to reducing potential, thus playing a role in maintaining the constitutive nitrogenase activity that facilitates the increased ammonia excretion of the disclosed engineered bacteria. In the exemplary ammonia-excreting mutants, transcription is driven by the inserted promoter in the opposite direction of the nifL/nifA genes (see FIG. 11), towards the rnf1 operon and in the rnf1 operon's direction of transcription. Accordingly, rnf1 expression should be upregulated in the disclosed ammonia-excreting mutants.

To demonstrate upregulation of rfn1 expression in the ammonia-excreting mutants, we performed quantitative real time RT-PCR to measure the expression of two selected genes from the rfn1 operon: rnfA1 and rnfD1. The results showed that both of these genes are up-regulated in the ΔnifL mutant ammonia excreting strains (~10×), relative to the wild type strain or the ΔnifL mutant strains that do not excrete ammonia.

In sum, these results confirm that the ammonia excretion phenotype, which includes both a deletion of the nifL gene and the insertion of a strong promoter sequence oriented in the opposite orientation of nifL/nifA transcription, exhibits the desired upregulation of rnf1 gene operon expression. Such upregulation acts to supply reduced Ferredoxin/Flavodoxin to feed the nitrogenase enzyme in low potential electrons, thus ensuring efficient nitrogen fixation.

Example 8: Determining Promoter Strength

The strength of the three promoter sequences referenced in Example 1, aph, cydAB, and cycB, was determined in vivo by measuring the β-galactosidase activity in strains carrying the $p_{aph}$_lacZ, $p_{cydAB}$_lacZ, and $p_{cycB}$_lacZ fusions. The lacZ gene from *Escherichia coli* placed under the transcriptional and translational control of aph, cydAB, and cycB promoters was inserted in *A. vinelandii* chromosome replacing scrX gene (Johnson et al., 2006).

Figure 12:
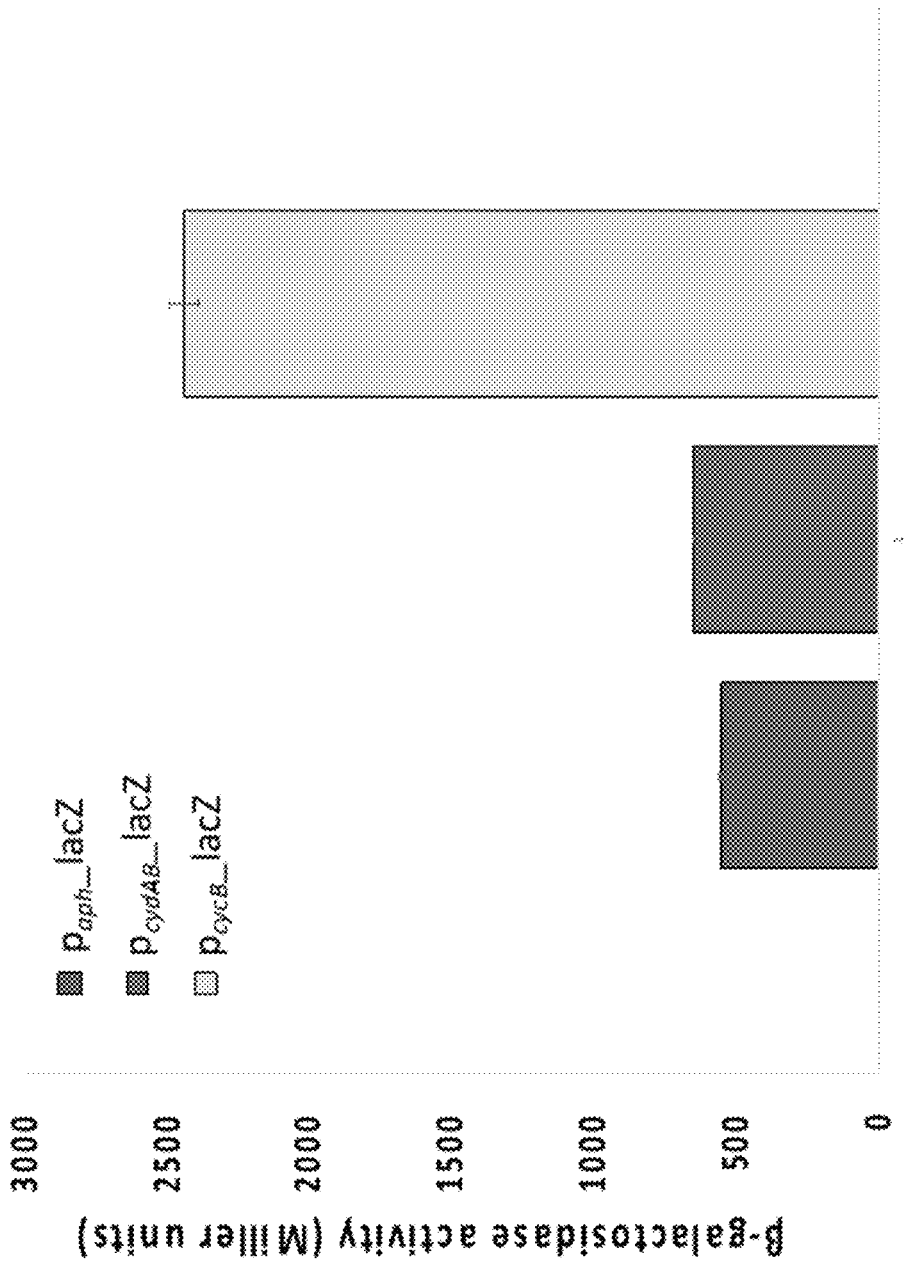
FIG. 12. A graph showing β-galactosidase activities of nifL mutants. Activity of $p_{aph}$-lacZ, $p_{cydAB}$-lacZ, and $p_{cydA}$-lacZ reporter in A. vinelandii under diazotrophic growth conditions. The results show the mean and standard deviation (error bars) for data from triplicate experiments.

As seen in FIG. 12, the β-galactosidase activity of the strain harboring the $p_{cycB}$_lacZ fusion was significantly higher compared to the strains harboring the $p_{aph}$_lacZ and the $p_{cydAB}$_lacZ fusion. The cycB promoter was upregulated around 4-fold relative to aph and cydAB promoters. The β-galactosidase activities of the strains harboring the $p_{aph}$_lacZ $p_{CydAB}$_lacZ fusions were similar, demonstrating that the expression of lacZ was not differentially regulated by aph and cydAB promoters.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

We claim:

1. A genetically modified diazotrophic γ-proteobacterium exhibiting an increased ability to fix atmospheric nitrogen, comprising:
   one or more insertions within the nifL gene of the wild type diazotrophic γ-proteobacterium, wherein the one or more insertions comprises a promoter sequence, and wherein the promoter sequence is placed and oriented to direct transcription of at least one gene of the rnf1 gene complex selected from the group consisting of rnfA1, rnfB1, rnfC1, rnfD1, rnfE1, rnfG1 and rnfH1 whereby the expression of the at least one gene of the rnf1 gene complex is upregulated relative to the wild type diazotrophic γ-proteobacterium;
   wherein the one or more insertions disrupts the nifL gene.

2. The genetically modified bacterium of claim 1, wherein the promoter sequence is oriented to direct transcription in the opposite direction of nifL/nifA transcription.

3. The genetically modified bacterium of claim 1, wherein the promoter is selected from cydA and cycB.

4. The genetically modified bacterium of claim 1, wherein the one or more insertions consist of a promoter sequence.

5. The genetically modified bacterium of claim 1, wherein the promoter sequence is a copy of a promoter sequence that is native to the wild type diazotrophic γ-proteobacterium, wherein the native promoter sequence occurs at a different location within the wild type diazotrophic γ-proteobacterium genome.

6. A bacterial culture comprising the genetically modified bacteria of claim 1, and a culture medium.

7. A biofertilizer composition comprising the bacterial culture of claim 6.

8. An agricultural system comprising the biofertilizer composition of claim 7 applied to soil.

9. The agricultural system of claim 8, wherein the soil is in contact with a plant or plant seed.

10. An agricultural system comprising the biofertilizer composition of claim 7 in contact with a plant or plant seed.

11. A method of stimulating plant growth by providing fixed nitrogen to the plant, comprising applying to the plant, a part of the plant, a seed of the plant, the soil in which the plant is planted, or the soil in which the plant it intend to be planted an effective amount of the biofertilizer composition of claim 7, whereby the plant takes up fixed nitrogen produced by the bacterial culture included in the biofertilizer composition, and the plant's growth is effective stimulated.

12. A bacterial/fungal co-culture comprising the bacterial culture of claim 6 and a fungal culture comprising mycorrhizal fungi.

13. A biofertilizer composition comprising the bacterial/fungal co-culture of claim 12.

14. A method of stimulating plant growth by providing fixed nitrogen to the plant, comprising applying to the plant, a part of the plant, a seed of the plant, the soil in which the plant is planted, or the soil in which the plant is intend to be planted an effective amount of the biofertilizer composition of claim 13, whereby the fungal culture included in the biofertilizer composition facilitates the transfer to the plant of the fixed nitrogen produced by the bacterial culture included in the biofertilizer composition, and the plant's growth is effectively stimulated.

15. The genetically modified bacterium of claim 1, wherein the one or more insertions further creates one or more deletions of a coding region of the nifL gene.

* * * * *

UNITED STATES PATENT AND TRADEMARK OFFICE
CERTIFICATE OF CORRECTION

PATENT NO. : 12,391,627 B2  
APPLICATION NO. : 17/024746  
DATED : August 19, 2025  
INVENTOR(S) : John Peters et al.

Page 1 of 2

It is certified that error appears in the above-identified patent and that said Letters Patent is hereby corrected as shown below:

In the Specification

Column 13, Lines 44-45, "$\Delta nifL:P_{aph}\_KIXX$" should be --$\Delta nifL::P_{aph}\_KIXX$--.

Column 17, Line 53, "KIXX/376" should be --KIXX/$\Delta$376--.

Column 19, Line 6, "4368" should be --$\Delta$368--.

Column 19, Line 47, "$\Delta$03" should be --403--.

Column 20, Line 41, "A376" should be --$\Delta$376--.

Column 20, Line 41, "4376" should be --$\Delta$376--.

Column 20, Line 50, "of 4376" should be --of $\Delta$376--.

Column 20, Line 50, "or 4376" should be --or $\Delta$376--.

Column 20, Line 56, "$nifL:p_{cydA}$ or $nifl:p_{cycB}$" should be --$nifL::p_{cydA}$ or $nifl::p_{cycB}$--.

Column 22, Line 13, "4376" should be --$\Delta$376--.

Column 22, Line 14, "4376" should be --$\Delta$376--.

Column 22, Line 21, "4376" should be --$\Delta$376--.

Column 23, Line 62, "$p_{aph}\_HIXX$" should be --$p_{aph}\_KIXX$--.

Signed and Sealed this  
Twentieth Day of January, 2026

John A. Squires  
*Director of the United States Patent and Trademark Office*

CERTIFICATE OF CORRECTION (continued)
U.S. Pat. No. 12,391,627 B2

Column 23, Line 67, "Ben" should be --BclI--.

Column 24, Line 4, "Ben" should be --BclI--.

Column 24, Line 61, "Ben" should be --BclI--.

Column 25, Line 27, "4346" should be --Δ376--.

Column 25, Line 28, "4346" should be --Δ376--.

Column 25, Line 34, "4346" should be --Δ376--.

Column 25, Line 37, "ΔnifL:" should be --ΔnifL::--.

Column 26, Line 19, "ΔnifL:$p_{aph}$_KIXX" should be --ΔnifL::$p_{aph}$_KIXX--.

Column 26, Line 35, "NdeUnifL371" should be --NdeI/nifL371--.

Column 27, Line 34, "0.25 g 0.5" should be --0.25 g liter$^{-1}$), 0.5--.

Column 27, Line 56, "Av376::$p_{aph}$ KIXX" should be --Av376::$p_{aph}$KIXX--.

Column 30, Line 57, "0.25 g 0.5" should be --0.25 g liter$^{-1}$), 0.5--.